US009556241B2

(12) United States Patent
Fiebig et al.

(10) Patent No.: US 9,556,241 B2
(45) Date of Patent: Jan. 31, 2017

(54) DNA SEQUENCE AND PREPARATION OF GRASS POLLEN ALLERGEN PHL P 4 BY RECOMBINANT METHODS

(71) Applicant: Merck Patent Gmbh, Darmstadt (DE)

(72) Inventors: Helmut Fiebig, Schwarzenbek (DE); Andreas Nandy, Hamburg (DE); Roland Suck, Hamburg (DE); Oliver Cromwell, Wentorf (DE); Arnd Petersen, Bad Segeberg (DE); Wolf-Meinhard Becker, Mozen (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/550,370

(22) Filed: Nov. 21, 2014

(65) Prior Publication Data

US 2015/0079120 A1 Mar. 19, 2015

Related U.S. Application Data

(62) Division of application No. 13/034,210, filed on Feb. 24, 2011, now Pat. No. 9,120,866, which is a division of application No. 10/518,927, filed as application No. PCT/EP03/06092 on Jun. 11, 2003, now Pat. No. 8,128,935.

(30) Foreign Application Priority Data

Jun. 25, 2002 (EP) .................................... 02013953

(51) Int. Cl.

| | |
|---|---|
| *A61K 39/00* | (2006.01) |
| *A61K 39/35* | (2006.01) |
| *A61K 39/36* | (2006.01) |
| *C07K 14/415* | (2006.01) |
| *G01N 33/68* | (2006.01) |
| *A61K 31/7088* | (2006.01) |
| *A61K 39/39* | (2006.01) |
| *A61K 45/06* | (2006.01) |
| *A61K 38/00* | (2006.01) |
| *A61K 48/00* | (2006.01) |

(52) U.S. Cl.
CPC ......... *C07K 14/415* (2013.01); *A61K 31/7088* (2013.01); *A61K 39/36* (2013.01); *A61K 39/39* (2013.01); *A61K 45/06* (2013.01); *G01N 33/6893* (2013.01); *A61K 38/00* (2013.01); *A61K 48/00* (2013.01); *G01N 2800/24* (2013.01)

(58) Field of Classification Search
None
See application file for complete search history.

(56) References Cited

U.S. PATENT DOCUMENTS

2003/0135888 A1 7/2003 Zhu et al.

OTHER PUBLICATIONS

Mukherjee et al. 'Allergic Asthma: Influence of Genetic and Environmental Factors.' The Journal of Biological Chemistry vol. 286(38):32883-32889, 2011.*
Zolkipli et al. 'Randomized controlled trial of primary prevention of atopy using house dust mite allergen oral immunotherapy in early childhood.' J. Allerg. Clin. Immunol. 136(6):1541-1547, 20015.*

Suck R et al: "The high molecular mass allergen fraction of timothy grass pollen (Phleum pratense) between50-60 kDa is comprised of two major allergens: Phl p4 and Phl p13"Clinical and Experimetnal Allergy, Bd. 30, Nr. 10, Oct. 2000, XP002260344.

Haavik et al. "Glycoprotein allergens in pollen of timothy. II. Isolation and characterization of a basic glycoprotein allergen." Int Arch Allergy Appl Immunol. 1985;78(3):260-8 (Abstract Only).
Fahlbusch B et al: Detection and quantification of group 4 allergens in grass pollen extracts using monoclonal antibodies Clinical and Experimental Allergy, Bd. 28, Nr. Jul. 7, 1998, 799-807, XP002260345.
Suck R et al: "Complementary DNA Cloning and expression of a newly recognized highmolecular mass allergen Phl P 13 from Timothy Grass pollen (Phleum pratense)" Clinical and experimental allergy, Blackwell scientific publications, London, GB, Bd. 30, Nr. 3, Mar. 2000, 324-332, XP000953168.

Stumvoll Sabine et al: "Purification, structural and immunological characterization of a timothy grass (Phleum pratense) pollen allergen, Phl p4, with cross-reactive potential." Bological Chemistry, Bd. 383, Nr. 9, Sep. 2002 1383-1396, XP002260346.

Valenta et al. "Diagnosis of Grass Pollen Allergy with Recombinant Timothy Grass (Phleum pretense) Pollen Allergens." Int Arch Allergy Immunol 1992;97:287-294. (Abstract Only).

Colman et al., "Effects of amino acid sequence changes on antibody-antigen interactions.", Research in Immunology 145 (1): pp. 33-36, 1994.

Abaza et al., Effects of amino acid substitutions outside an antigenic site on protein binding of monoclonal antibodies of predetermined specificity obtained by peptide immunication . . . , J. Prot. Chem., 11 (5): pp. 433-444, 1992.

Ledermnan et al., "A single amino acid substitution in a common African allele of the CD4 molecule ablates binding of the monoclonal antibody", OKT4, Molec. Immunolo 28: pp. 1171-1181, 1991.

Blumenthal et al., "Definition of an Allergen", Allergens and Allergen Immunotherapy, New York: Marcel Decker, p. 37-50, 2004.

Fischer et al., "Characterization of Phl. P. 4, major timothy grass (Phleum pretense) pollen allergen", J. Allerg. Clin. Immunol. 98 (1): pp. 189-198, 1996.

(Continued)

*Primary Examiner* — Nora Rooney

(74) *Attorney, Agent, or Firm* — Miller, White, Zelano, Branigan, P.C.

(57) ABSTRACT

The present invention relates to the preparation and use of recombinant variants of group 6 allergens of the *Poaceae* (true grasses), which are characterized by reduced IgE reactivity compared with known wild-type allergens and at the same time substantially retained reactivity with T-lymphocytes.

3 Claims, 5 Drawing Sheets

(56) References Cited

OTHER PUBLICATIONS

Kinnunen et al., "Potential of an altered peptide ligand of lipocalin allergen Bos d 2 for peptide immunotherapy", J. Allergy clin. Immunol., 119 (4): pp. 965-972, 2007.
Tarzi et al., "Peptide immunotherapy for allergic disease", Expert. Opin. Biol. Ther. 3 (4): pp. 617-626, 2003.
Metzler et al., "Solution structure of human CTLA-4 and delineation of a CD80/CD86 binding site conserved in CD28", Nature Structural Biol. 4: pp. 527-531, 1997.
Bowie et al., "Deciphering the message in protein sequences: tolerance to amino acid substitutions", Science, 247: pp. 1306-1310, 1990.
Kuby et al., "Immunology", Fourth Edition, Chapter 18: pp. 449-465.

\* cited by examiner

Fig. 1    Internal DNA sequence of the Phl p 4 gene

```
C A C C G G A A G G G G G G T G C T G T T C A A C A T C C A G T A C G T C A A
C T A C T G G T T C G C C C C G G G A G C C G G C G C G G C G C C A T T G T
C G T G G A G C A A G G A G A T C T A C A A C T A C A T G G A G C C G T A C
G T G A G C A A G G A C C C C G T C C A G G C C T A C G C C A A C T A
```

Fig. 2    3' end of the nucleic acid sequence of the Phl p 4 gene

```
A C T A C T G G T T C G C C C C G G G A G C C G G C G C G G C
G C C A T T G T C G T G G A G C A A G G A G A T C T A C A A C
T A C A T G G A G C C A T A C G T G A G C A A G A A C C C C A
G G C A G G C C T A C G C C A A C T A C A G G G A C A T C G A
C C T C G G G A G G A A C G A G G T G G T G A A C G A C G T C
T C C A C C T T C A G C A G C G G T T T G G T G T G G G G C C
A G A A A T A C T T C A A G G G C A A C T T C C A G A G G C T
C G C C A T C A C C A A G G G C A A G G T G G A T C C C A C C
G A C T A C T T C A G G A A C G A G C A G A G C A T C C C G C
C G C T C A T C A A A A A G T A C T G A
```

Fig. 3  Localisation of Phl p 4 peptides in the deduced amino acid sequence of the Phl p 4 allergen

```
1   Y F P P P A A K E D F L G C L V K E I P P R L L Y A K S S P A Y P S V L G Q T I
    Y F P P P A A K E D F L G X L V K E I P P R L L Y A K S S P A Y P
                                Peptide P1

41  R N S R W S S P D N V K P I Y I V T P T N A S H I Q S A V V C G R R H G V R I R

81  V R S G G H D Y E G L S Y R S L Q P E E F A V V D L S K M R A V W V D G K A R T
                                G L X Y R X L X P E
                                Peptide P3

121 A W V D S G A Q L G E L Y Y A I H K A S T V L A F P A G V C P T I G V G G N F A

161 G G G F G M L L R K Y G I A A E N V I D V K L V D A N G T L H D K K S M G D D H
                                                                    K X M G D D H
                                                                    Peptide P4

201 F W A V R G G G E S F G I V V A W K V R L L P V P P T V T V F K I P K K A S E
    F X A V R                                                             A P E

241 G A V D I I N R W Q V V A P Q L P D D L M I R V I A Q G P T A T F E A M Y L G T
    G A V D I I
    Peptide P5

281 C Q T L T P M M S S K F P E L G M N A S H C N E M S W I Q S I P F V H L G H R D

321 N I E D D L L N R N N T F K P F A E Y K S D Y V Y E P F P K R V W E Q I F S T W

361 L L K P G A G I M I F D P Y G A T I S A T P E W A T P F P H R K G V L F N I Q Y
                                      S A T P F X H R K G V L F N I Q Y
                                                    Peptide P2

401 V N Y W F A P G A G A A P L S W S K E I I N Y M E P Y V S K N P R Q A Y A N Y R
    V                                           M E P Y V S I N P V Q A Y A N Y
                                                            Peptide P6

441 D I D L G R N E V V N D V S T F S S G L V W G Q K Y F K G N F Q R L A I T K G K

481 V D P T D Y F R N E Q S I P P L I K K Y .
```

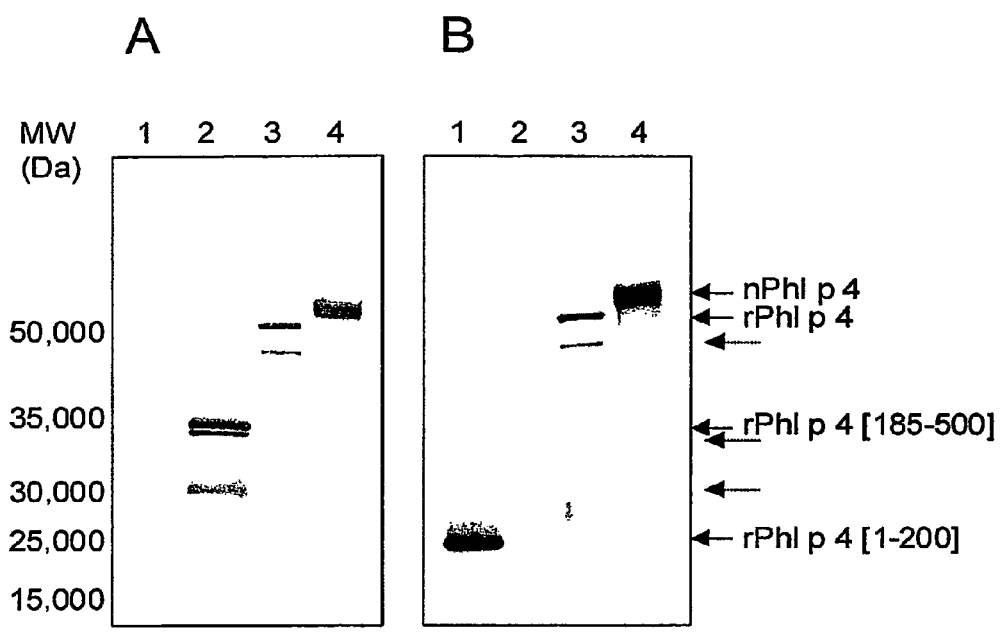
Fig. 4　Determination of the identity of recombinant Phl p 4 (rPhl p 4) by means of the monoclonal antibodies 5H1 (blot A) and 3C4 (blot B) by Western blot Fig. 5    Determination of the reactivity of recombinant Phl p 4
(rPhl p 4) with IgE from sera of grass pollen allergy
sufferers by Western blot
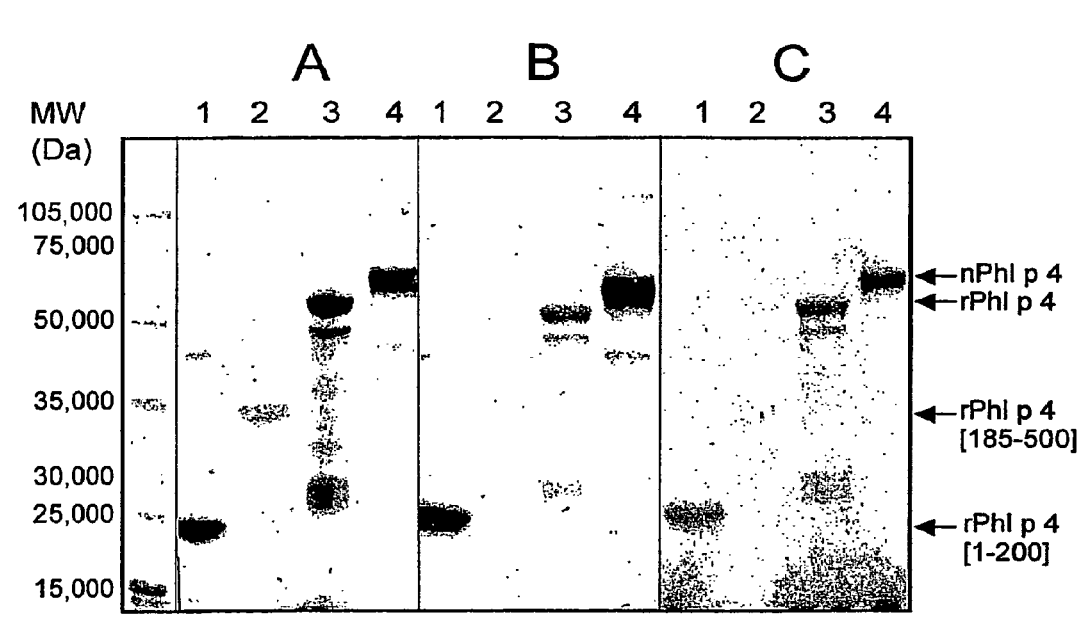

SEQUENCE LISTING

```
<160> NUMBER OF SEQ ID NOS: 52

<210> SEQ ID NO 1
<211> LENGTH: 1503
<212> TYPE: DNA
<213> ORGANISM: Phleum pratense
<220> FEATURE:
<221> NAME/KEY: artificial_DNA_sequence
<222> LOCATION: (1)..(69)
<223> OTHER INFORMATION: DNA sequence derived from sequenced protein
<220> FEATURE:
<221> NAME/KEY: native_DNA_sequence
<222> LOCATION: (70)..(1503)
<223> OTHER INFORMATION:
<220> FEATURE:
<221> NAME/KEY: CDS
<222> LOCATION: (1)..(1503)
<223> OTHER INFORMATION:

<400> SEQUENCE: 1 tac ttc ccg ccg ccg gct gct aaa gaa gac ttc ctg ggt tgc ctg gtt      48
Tyr Phe Pro Pro Pro Ala Ala Lys Glu Asp Phe Leu Gly Cys Leu Val
1               5                   10                  15 aaa gaa atc ccg ccg cgt ctg ttg tac gcg aaa tcg tcg ccg gcg tat      96
Lys Glu Ile Pro Pro Arg Leu Leu Tyr Ala Lys Ser Ser Pro Ala Tyr
                20                  25                  30 ccc tca gtc ctg ggg cag acc atc cgg aac tcg cgg tgg tcg tcg ccg     144
Pro Ser Val Leu Gly Gln Thr Ile Arg Asn Ser Arg Trp Ser Ser Pro
            35                  40                  45 gac aac gtg aag ccg atc tac atc gtc acc ccc acc aac gcc tcc cac     192
Asp Asn Val Lys Pro Ile Tyr Ile Val Thr Pro Thr Asn Ala Ser His
        50                  55                  60 atc cag tcc gcc gtg gtg tgc ggc cgc cgg cac ggt gtc cgc atc cgc     240
Ile Gln Ser Ala Val Val Cys Gly Arg Arg His Gly Val Arg Ile Arg
65                  70                  75                  80 gtg cgc agc ggc ggg cac gac tac gag ggc ctc tcg tac cgg tcc ctg     288
Val Arg Ser Gly Gly His Asp Tyr Glu Gly Leu Ser Tyr Arg Ser Leu
                85                  90                  95 cag ccc gag gag ttc gcc gtc gtc gac ctt agc aag atg cgg gcc gtg     336
Gln Pro Glu Glu Phe Ala Val Val Asp Leu Ser Lys Met Arg Ala Val
            100                 105                 110 tgg gtg gac ggg aag gcc cgc acg gcg tgg gtc gac tcc ggc gcg cag     384
Trp Val Asp Gly Lys Ala Arg Thr Ala Trp Val Asp Ser Gly Ala Gln
        115                 120                 125 ctc ggc gag ctc tac tac gcc atc cac aag gcg agt aca gtg ctg gcg     432
```

|   |   |   |   |   |   |   |   |   |   |   |   |   |   |   |   |   |
|---|---|---|---|---|---|---|---|---|---|---|---|---|---|---|---|---|
| Leu | Gly | Glu | Leu | Tyr | Tyr | Ala | Ile | His | Lys | Ala | Ser | Thr | Val | Leu | Ala | |
| | 130 | | | | | 135 | | | | 140 | | | | | | |

```
ttc ccg gcc ggc gtg tgc ccg acc atc ggc gtg ggc ggc aac ttc gcg        480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcg gcc gag        528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc acg ctg cac gac        576
Asn Val Ile Asp Val Lys Leu Val Asp Ala Asn Gly Thr Leu His Asp
            180                 185                 190 aag aag tcc atg ggc gac gac cat ttc tgg gcc gtc agg ggc ggc ggg        624
Lys Lys Ser Met Gly Asp Asp His Phe Trp Ala Val Arg Gly Gly Gly
        195                 200                 205 ggc gag agc ttc ggc atc gtg gtc gcg tgg aag gtg agg ctc ctg ccg        672
Gly Glu Ser Phe Gly Ile Val Val Ala Trp Lys Val Arg Leu Leu Pro
    210                 215                 220 gtg ccg ccc acg gtg acc gtg ttc aag atc ccc aag aag gcg agc gag        720
Val Pro Pro Thr Val Thr Val Phe Lys Ile Pro Lys Lys Ala Ser Glu
225                 230                 235                 240 ggc gcc gtg gac atc atc aac agg tgg cag gtg gtc gcg ccg cag ctc        768
Gly Ala Val Asp Ile Ile Asn Arg Trp Gln Val Val Ala Pro Gln Leu
                245                 250                 255 ccc gac gac ctc atg atc cgc gtc atc gcg cag ggc ccc acg gcc acg        816
Pro Asp Asp Leu Met Ile Arg Val Ile Ala Gln Gly Pro Thr Ala Thr
            260                 265                 270 ttc gag gcc atg tac ctg ggc acc tgc caa acc ctg acg ccg atg atg        864
Phe Glu Ala Met Tyr Leu Gly Thr Cys Gln Thr Leu Thr Pro Met Met
        275                 280                 285 agc agc aag ttc ccg gag ctc ggc atg aac gcc tcg cac tgc aac gag        912
Ser Ser Lys Phe Pro Glu Leu Gly Met Asn Ala Ser His Cys Asn Glu
    290                 295                 300 atg tcg tgg atc cag tcc atc ccc ttc gtc cac ctc ggc cac agg gac        960
Met Ser Trp Ile Gln Ser Ile Pro Phe Val His Leu Gly His Arg Asp
305                 310                 315                 320 aac atc gag gac gac ctc ctc aac cgg aac aac acc ttc aag ccc ttc       1008
Asn Ile Glu Asp Asp Leu Leu Asn Arg Asn Asn Thr Phe Lys Pro Phe
                325                 330                 335 gcc gaa tac aag tcg gac tac gtc tac gag ccg ttc ccc aag agg gtg       1056
Ala Glu Tyr Lys Ser Asp Tyr Val Tyr Glu Pro Phe Pro Lys Arg Val
            340                 345                 350 tgg gag cag atc ttc agc acc tgg ctc ctg aag ccc ggc gcg ggg atc       1104
Trp Glu Gln Ile Phe Ser Thr Trp Leu Leu Lys Pro Gly Ala Gly Ile
        355                 360                 365 atg atc ttc gac ccc tac ggc gcc acc atc agc gcc acc ccg gag tgg       1152
Met Ile Phe Asp Pro Tyr Gly Ala Thr Ile Ser Ala Thr Pro Glu Trp
    370                 375                 380 gcg acg ccg ttc cct cac cgc aag ggc gtc ctc ttc aac atc cag tac       1200
Ala Thr Pro Phe Pro His Arg Lys Gly Val Leu Phe Asn Ile Gln Tyr
385                 390                 395                 400 gtc aac tac tgg ttc gcc ccg gga gcc ggc gcg gcg cca ttg tcg tgg       1248
Val Asn Tyr Trp Phe Ala Pro Gly Ala Gly Ala Ala Pro Leu Ser Trp
                405                 410                 415 agc aag gag atc tac aac tac atg gag cca tac gtg agc aag aac ccc       1296
Ser Lys Glu Ile Tyr Asn Tyr Met Glu Pro Tyr Val Ser Lys Asn Pro
            420                 425                 430 agg cag gcc tac gcc aac tac agg gac atc gac ctc ggg agg aac gag       1344
Arg Gln Ala Tyr Ala Asn Tyr Arg Asp Ile Asp Leu Gly Arg Asn Glu
        435                 440                 445
```

```
gtg gtg aac gac gtc tcc acc ttc agc agc ggt ttg gtg tgg ggc cag      1392
Val Val Asn Asp Val Ser Thr Phe Ser Ser Gly Leu Val Trp Gly Gln
450                 455                 460 aaa tac ttc aag ggc aat ttc cag agg ctc gcc atc acc aag ggc aag      1440
Lys Tyr Phe Lys Gly Asn Phe Gln Arg Leu Ala Ile Thr Lys Gly Lys
465                 470                 475                 480 gtg gat ccc acc gac tac ttc agg aac gag cag agc atc ccg ccg ctc      1488
Val Asp Pro Thr Asp Tyr Phe Arg Asn Glu Gln Ser Ile Pro Pro Leu
                485                 490                 495 atc aaa aag tac tga                                                  1503
Ile Lys Lys Tyr
500
```

<210> SEQ ID NO 2
<211> LENGTH: 500
<212> TYPE: PRT
<213> ORGANISM: Phleum pratense

<400> SEQUENCE: 2

```
Tyr Phe Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
                20                  25                  30

Pro Ser Val Leu Gly Gln Thr Ile Arg Asn Ser Arg Trp Ser Ser Pro
            35                  40                  45

Asp Asn Val Lys Pro Ile Tyr Ile Val Thr Pro Thr Asn Ala Ser His
        50                  55                  60

Ile Gln Ser Ala Val Val Cys Gly Arg Arg His Gly Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Glu Phe Ala Val Val Asp Leu Ser Lys Met Arg Ala Val
            100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile His Lys Ala Ser Thr Val Leu Ala
130                 135                 140

Phe Pro Ala Gly Val Cys Pro Thr Ile Gly Val Gly Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Thr Leu His Asp
            180                 185                 190

Lys Lys Ser Met Gly Asp Asp His Phe Trp Ala Val Arg Gly Gly Gly
        195                 200                 205

Gly Glu Ser Phe Gly Ile Val Val Ala Trp Lys Val Arg Leu Leu Pro
210                 215                 220

Val Pro Pro Thr Val Thr Val Phe Lys Ile Pro Lys Lys Ala Ser Glu
225                 230                 235                 240

Gly Ala Val Asp Ile Ile Asn Arg Trp Gln Val Val Ala Pro Gln Leu
                245                 250                 255

Pro Asp Asp Leu Met Ile Arg Val Ile Ala Gln Gly Pro Thr Ala Thr
            260                 265                 270

Phe Glu Ala Met Tyr Leu Gly Thr Cys Gln Thr Leu Thr Pro Met Met
        275                 280                 285

Ser Ser Lys Phe Pro Glu Leu Gly Met Asn Ala Ser His Cys Asn Glu
```

```
                    290                 295                 300
Met Ser Trp Ile Gln Ser Ile Pro Phe Val His Leu Gly His Arg Asp
305                 310                 315                 320

Asn Ile Glu Asp Asp Leu Leu Asn Arg Asn Asn Thr Phe Lys Pro Phe
                325                 330                 335

Ala Glu Tyr Lys Ser Asp Tyr Val Tyr Glu Pro Phe Pro Lys Arg Val
                340                 345                 350

Trp Glu Gln Ile Phe Ser Thr Trp Leu Leu Lys Pro Gly Ala Gly Ile
            355                 360                 365

Met Ile Phe Asp Pro Tyr Gly Ala Thr Ile Ser Ala Thr Pro Glu Trp
        370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Gly Ala Ala Pro Leu Ser Trp
                405                 410                 415

Ser Lys Glu Ile Tyr Asn Tyr Met Glu Pro Tyr Val Ser Lys Asn Pro
                420                 425                 430

Arg Gln Ala Tyr Ala Asn Tyr Arg Asp Ile Asp Leu Gly Arg Asn Glu
            435                 440                 445

Val Val Asn Asp Val Ser Thr Phe Ser Ser Gly Leu Val Trp Gly Gln
        450                 455                 460

Lys Tyr Phe Lys Gly Asn Phe Gln Arg Leu Ala Ile Thr Lys Gly Lys
465                 470                 475                 480

Val Asp Pro Thr Asp Tyr Phe Arg Asn Glu Gln Ser Ile Pro Leu
                485                 490                 495

Ile Lys Lys Tyr
            500

<210> SEQ ID NO 3
<211> LENGTH: 1503
<212> TYPE: DNA
<213> ORGANISM: Phleum pratense
<220> FEATURE:
<221> NAME/KEY: artificial_DNA_sequence
<222> LOCATION: (1)..(69)
<223> OTHER INFORMATION: DNA sequence derived from sequenced protein
<220> FEATURE:
<221> NAME/KEY: native_DNA_sequence
<222> LOCATION: (70)..(1503)
<223> OTHER INFORMATION:
<220> FEATURE:
<221> NAME/KEY: CDS
<222> LOCATION: (1)..(1503)
<223> OTHER INFORMATION:

<400> SEQUENCE: 3 tac ttc ccg ccg ccg gct gct aaa gaa gac ttc ctg ggt tgc ctg gtt     48
Tyr Phe Pro Pro Pro Ala Ala Lys Glu Asp Phe Leu Gly Cys Leu Val
1               5                   10                  15 aaa gaa atc ccg ccg cgt ctg ttg tac gcg aaa tcg tcg ccg gcg tat     96
Lys Glu Ile Pro Pro Arg Leu Leu Tyr Ala Lys Ser Ser Pro Ala Tyr
            20                  25                  30 ccc tca gtc ctg ggg cag acc atc cgg aac tcg cgg tgg tcg tcg ccg    144
Pro Ser Val Leu Gly Gln Thr Ile Arg Asn Ser Arg Trp Ser Ser Pro
        35                  40                  45 gac aac gtg aag ccg atc tac atc gtc acc ccc acc aac gcc tcc cac    192
Asp Asn Val Lys Pro Ile Tyr Ile Val Thr Pro Thr Asn Ala Ser His
    50                  55                  60 atc cag tcc gcc gtg gtg tgc ggc cgc cgg cac ggt gtc cgc atc cgc    240
Ile Gln Ser Ala Val Val Cys Gly Arg Arg His Gly Val Arg Ile Arg
```

-continued

| | |
|---|---|
| gtg cgc agc ggc ggg cac gac tac gag ggc ctc tcg tac cgg tcc ctg<br>Val Arg Ser Gly Gly His Asp Tyr Glu Gly Leu Ser Tyr Arg Ser Leu<br>                85                        90                  95 | 288 |
| cag ccc gag gag ttc gcc gtc gtc gac ctt agc aag atg cgg gcc gtg<br>Gln Pro Glu Glu Phe Ala Val Val Asp Leu Ser Lys Met Arg Ala Val<br>            100                    105                  110 | 336 |
| tgg gtg gac ggg aag gcc cgc acg gcg tgg gtc gac tcc ggc gcg cag<br>Trp Val Asp Gly Lys Ala Arg Thr Ala Trp Val Asp Ser Gly Ala Gln<br>            115                    120                  125 | 384 |
| ctc ggc gag ctc tac tac gcc atc cac aag gcg agt cca gtg ctg gcg<br>Leu Gly Glu Leu Tyr Tyr Ala Ile His Lys Ala Ser Pro Val Leu Ala<br>130                    135                    140 | 432 |
| ttc ccg gcc ggc gtg tgc ccg acc atc ggc gtg ggc ggc aac ttc gcg<br>Phe Pro Ala Gly Val Cys Pro Thr Ile Gly Val Gly Gly Asn Phe Ala<br>145                    150                    155                  160 | 480 |
| ggc ggc ggc ttc ggc atg ctg ctg cgc aag tac ggc atc gcg gcc gag<br>Gly Gly Gly Phe Gly Met Leu Leu Arg Lys Tyr Gly Ile Ala Ala Glu<br>                  165                    170                  175 | 528 |
| aac gtc atc gac gtg aag ctc gtc gac gcc aac ggc acg ctg cac gac<br>Asn Val Ile Asp Val Lys Leu Val Asp Ala Asn Gly Thr Leu His Asp<br>            180                    185                  190 | 576 |
| aag aag tcc atg ggc gac gac cat ttc tgg gcc gtc agg ggc ggc ggg<br>Lys Lys Ser Met Gly Asp Asp His Phe Trp Ala Val Arg Gly Gly Gly<br>            195                    200                  205 | 624 |
| ggc gag agc ttc ggc atc gtg gtc gcg tgg aag gtg agg ctc ctg ccg<br>Gly Glu Ser Phe Gly Ile Val Val Ala Trp Lys Val Arg Leu Leu Pro<br>            210                    215                  220 | 672 |
| gtg ccg ccc acg gtg acc gtg ttc aag atc ccc aag aag gcg agc gag<br>Val Pro Pro Thr Val Thr Val Phe Lys Ile Pro Lys Lys Ala Ser Glu<br>225                    230                    235                  240 | 720 |
| ggc gcc gtg gac atc atc aac agg tgg cag gtg gtc gcg ccg cag ctc<br>Gly Ala Val Asp Ile Ile Asn Arg Trp Gln Val Val Ala Pro Gln Leu<br>                  245                    250                  255 | 768 |
| ccc gac gac ctc atg atc cgc gtc atc gcg cag ggc ccc acg gcc acg<br>Pro Asp Asp Leu Met Ile Arg Val Ile Ala Gln Gly Pro Thr Ala Thr<br>            260                    265                  270 | 816 |
| ttc gag gcc atg tac ctg ggc acc tgc caa acc ctg acg ccg atg atg<br>Phe Glu Ala Met Tyr Leu Gly Thr Cys Gln Thr Leu Thr Pro Met Met<br>              275                    280                  285 | 864 |
| agc agc aag ttc ccc gag ctc ggc atg aac gcc tcg cac tgc aac gag<br>Ser Ser Lys Phe Pro Glu Leu Gly Met Asn Ala Ser His Cys Asn Glu<br>            290                    295                  300 | 912 |
| atg tcg tgg atc cag tcc atc ccc ttc gtc cac ctc ggc cac agg gac<br>Met Ser Trp Ile Gln Ser Ile Pro Phe Val His Leu Gly His Arg Asp<br>305                    310                    315                  320 | 960 |
| aac atc gag gac gac ctc ctc aac cgg aac aac acc ttc aag ccc ttc<br>Asn Ile Glu Asp Asp Leu Leu Asn Arg Asn Asn Thr Phe Lys Pro Phe<br>                  325                    330                  335 | 1008 |
| gcc gaa tac aag tcg gac tac gtc tac gag ccg ttc ccc aag gaa gtg<br>Ala Glu Tyr Lys Ser Asp Tyr Val Tyr Glu Pro Phe Pro Lys Glu Val<br>            340                    345                  350 | 1056 |
| tgg gag cag atc ttc agc acc tgg ctc ctg aag ccc ggc gcg ggg atc<br>Trp Glu Gln Ile Phe Ser Thr Trp Leu Leu Lys Pro Gly Ala Gly Ile<br>            355                    360                  365 | 1104 |
| atg atc ttc gac ccc tac ggc gcc acc atc agc gcc acc ccg gag tgg<br>Met Ile Phe Asp Pro Tyr Gly Ala Thr Ile Ser Ala Thr Pro Glu Trp<br>370                    375                    380 | 1152 |
| gcg acg ccg ttc cct cac cgc aag ggc gtc ctc ttc aac atc cag tac | 1200 |

```
Ala Thr Pro Phe Pro His Arg Lys Gly Val Leu Phe Asn Ile Gln Tyr
385                 390                 395                 400 gtc aac tac tgg ttc gcc ccg gga gcc ggc gcg gcg cca ttg tcg tgg     1248
Val Asn Tyr Trp Phe Ala Pro Gly Ala Gly Ala Ala Pro Leu Ser Trp
                    405                 410                 415 agc aag gag atc tac aac tac atg gag cca tac gtg agc aag aac ccc     1296
Ser Lys Glu Ile Tyr Asn Tyr Met Glu Pro Tyr Val Ser Lys Asn Pro
                420                 425                 430 agg cag gcc tac gcc aac tac agg gac atc gac ctc ggg agg aac gag     1344
Arg Gln Ala Tyr Ala Asn Tyr Arg Asp Ile Asp Leu Gly Arg Asn Glu
            435                 440                 445 gtg gtg aac gac gtc tcc acc ttc agc agc ggt ttg gtg tgg ggc cag     1392
Val Val Asn Asp Val Ser Thr Phe Ser Ser Gly Leu Val Trp Gly Gln
        450                 455                 460 aaa tac ttc aag ggc aat ttc cag agg ctc gcc atc acc aag ggc aag     1440
Lys Tyr Phe Lys Gly Asn Phe Gln Arg Leu Ala Ile Thr Lys Gly Lys
465                 470                 475                 480 gtg gat ccc acc gac tac ttc agg aac gag cag agc atc ccg ccg ctc     1488
Val Asp Pro Thr Asp Tyr Phe Arg Asn Glu Gln Ser Ile Pro Pro Leu
                485                 490                 495 atc aaa aag tac tga                                                  1503
Ile Lys Lys Tyr
                500

<210> SEQ ID NO 4
<211> LENGTH: 500
<212> TYPE: PRT
<213> ORGANISM: Phleum pratense

<400> SEQUENCE: 4

Tyr Phe Pro Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
                20                  25                  30

Pro Ser Val Leu Gly Gln Thr Ile Arg Asn Ser Arg Trp Ser Ser Pro
            35                  40                  45

Asp Asn Val Lys Pro Ile Tyr Ile Val Thr Pro Thr Asn Ala Ser His
50                  55                  60

Ile Gln Ser Ala Val Val Cys Gly Arg His Gly Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Glu Phe Ala Val Val Asp Leu Ser Lys Met Arg Ala Val
            100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile His Lys Ala Ser Pro Val Leu Ala
130                 135                 140

Phe Pro Ala Gly Val Cys Pro Thr Ile Gly Val Gly Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Thr Leu His Asp
            180                 185                 190

Lys Lys Ser Met Gly Asp Asp His Phe Trp Ala Val Arg Gly Gly Gly
        195                 200                 205

Gly Glu Ser Phe Gly Ile Val Val Ala Trp Lys Val Arg Leu Leu Pro
```

```
                   210                 215                 220
Val Pro Pro Thr Val Thr Val Phe Lys Ile Pro Lys Lys Ala Ser Glu
225                 230                 235                 240

Gly Ala Val Asp Ile Ile Asn Arg Trp Gln Val Val Ala Pro Gln Leu
                245                 250                 255

Pro Asp Asp Leu Met Ile Arg Val Ile Ala Gln Gly Pro Thr Ala Thr
                    260                 265                 270

Phe Glu Ala Met Tyr Leu Gly Thr Cys Gln Thr Leu Thr Pro Met Met
            275                 280                 285

Ser Ser Lys Phe Pro Glu Leu Gly Met Asn Ala Ser His Cys Asn Glu
        290                 295                 300

Met Ser Trp Ile Gln Ser Ile Pro Phe Val His Leu Gly His Arg Asp
305                 310                 315                 320

Asn Ile Glu Asp Asp Leu Leu Asn Arg Asn Asn Thr Phe Lys Pro Phe
                    325                 330                 335

Ala Glu Tyr Lys Ser Asp Tyr Val Tyr Glu Pro Phe Pro Lys Glu Val
                340                 345                 350

Trp Glu Gln Ile Phe Ser Thr Trp Leu Leu Lys Pro Gly Ala Gly Ile
            355                 360                 365

Met Ile Phe Asp Pro Tyr Gly Ala Thr Ile Ser Ala Thr Pro Glu Trp
        370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Gly Ala Ala Pro Leu Ser Trp
                    405                 410                 415

Ser Lys Glu Ile Tyr Asn Tyr Met Glu Pro Tyr Val Ser Lys Asn Pro
                420                 425                 430

Arg Gln Ala Tyr Ala Asn Tyr Arg Asp Ile Asp Leu Gly Arg Asn Glu
            435                 440                 445

Val Val Asn Asp Val Ser Thr Phe Ser Ser Gly Leu Val Trp Gly Gln
        450                 455                 460

Lys Tyr Phe Lys Gly Asn Phe Gln Arg Leu Ala Ile Thr Lys Gly Lys
465                 470                 475                 480

Val Asp Pro Thr Asp Tyr Phe Arg Asn Glu Gln Ser Ile Pro Pro Leu
                    485                 490                 495

Ile Lys Lys Tyr
            500

<210> SEQ ID NO 5
<211> LENGTH: 1503
<212> TYPE: DNA
<213> ORGANISM: Phleum pratense
<220> FEATURE:
<221> NAME/KEY: artificial_DNA_sequence
<222> LOCATION: (1)..(69)
<223> OTHER INFORMATION: DNA sequence derived from sequenced protein
<220> FEATURE:
<221> NAME/KEY: native_DNA_sequence
<222> LOCATION: (70)..(1503)
<223> OTHER INFORMATION:
<220> FEATURE:
<221> NAME/KEY: CDS
<222> LOCATION: (1)..(1503)
<223> OTHER INFORMATION:

<400> SEQUENCE: 5 tac ttc ccg ccg ccg gct gct aaa gaa gac ttc ctg ggt tgc ctg gtt     48
Tyr Phe Pro Pro Pro Ala Ala Lys Glu Asp Phe Leu Gly Cys Leu Val
1               5                   10                  15
```

```
aaa gaa atc ccg ccg cgt ctg ttg tac gcg aaa tcg tcg ccg gcg tat       96
Lys Glu Ile Pro Pro Arg Leu Leu Tyr Ala Lys Ser Ser Pro Ala Tyr
         20                  25                  30 ccc tca gtc ctg ggg cag acc atc cgg aac tcg agg tgg tcg tcg ccg      144
Pro Ser Val Leu Gly Gln Thr Ile Arg Asn Ser Arg Trp Ser Ser Pro
     35                  40                  45 gac aac gtg aag ccg ctc tac atc atc acc ccc acc aac gtc tcc cac      192
Asp Asn Val Lys Pro Leu Tyr Ile Ile Thr Pro Thr Asn Val Ser His
 50                  55                  60 atc cag tcc gcc gtg gtg tgc ggc cgc cgc cac agc gtc cgc atc cgc      240
Ile Gln Ser Ala Val Val Cys Gly Arg Arg His Ser Val Arg Ile Arg
65                  70                  75                  80 gtg cgc agc ggc ggg cac gac tac gag ggc ctc tcg tac cgg tct ttg      288
Val Arg Ser Gly Gly His Asp Tyr Glu Gly Leu Ser Tyr Arg Ser Leu
                 85                  90                  95 cag ccc gag acg ttc gcc gtc gtc gac ctc aac aag atg cgg gcg gtg      336
Gln Pro Glu Thr Phe Ala Val Val Asp Leu Asn Lys Met Arg Ala Val
             100                 105                 110 tgg gtg gac ggc aag gcc cgc acg gcg tgg gtg gac tcc ggc gcg cag      384
Trp Val Asp Gly Lys Ala Arg Thr Ala Trp Val Asp Ser Gly Ala Gln
         115                 120                 125 ctc ggc gag ctc tac tac gcc atc tat aag gcg agc ccc acg ctg gcg      432
Leu Gly Glu Leu Tyr Tyr Ala Ile Tyr Lys Ala Ser Pro Thr Leu Ala
     130                 135                 140 ttc ccg gcc ggc gtg tgc ccg acg atc gga gtg ggc ggc aac ttc gcg      480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcc gcg gag      528
Gly Gly Gly Phe Gly Met Leu Leu Arg Lys Tyr Gly Ile Ala Ala Glu
                 165                 170                 175 aac gtc atc gac gtg aag ctc gtc gac gcc aac ggc aag ctg cac gac      576
Asn Val Ile Asp Val Lys Leu Val Asp Ala Asn Gly Lys Leu His Asp
             180                 185                 190 aag aag tcc atg ggc gac gac cat ttc tgg gcc gtc agg ggc ggc ggg      624
Lys Lys Ser Met Gly Asp Asp His Phe Trp Ala Val Arg Gly Gly Gly
         195                 200                 205 ggc gag agc ttc ggc atc gtg gtc gcg tgg cag gtg aag ctc ctg ccg      672
Gly Glu Ser Phe Gly Ile Val Val Ala Trp Gln Val Lys Leu Leu Pro
     210                 215                 220 gtg ccg ccc acc gtg aca ata ttc aag atc tcc aag aca gtg agc gag      720
Val Pro Pro Thr Val Thr Ile Phe Lys Ile Ser Lys Thr Val Ser Glu
225                 230                 235                 240 ggc gcc gtg gac atc atc aac aag tgg caa gtg gtc gcg ccg cag ctt      768
Gly Ala Val Asp Ile Ile Asn Lys Trp Gln Val Val Ala Pro Gln Leu
                 245                 250                 255 ccc gcc gac ctc atg atc cgc atc atc gcg cag ggg ccc aag gcc acg      816
Pro Ala Asp Leu Met Ile Arg Ile Ile Ala Gln Gly Pro Lys Ala Thr
             260                 265                 270 ttc gag gcc atg tac ctc ggc acc tgc aaa acc ctg acg ccg ttg atg      864
Phe Glu Ala Met Tyr Leu Gly Thr Cys Lys Thr Leu Thr Pro Leu Met
         275                 280                 285 agc agc aag ttc ccg gag ctc ggc atg aac ccc tcc cac tgc aac gag      912
Ser Ser Lys Phe Pro Glu Leu Gly Met Asn Pro Ser His Cys Asn Glu
     290                 295                 300 atg tca tgg atc cag tcc atc ccc ttc gtc cac ctc ggc cac agg gac      960
Met Ser Trp Ile Gln Ser Ile Pro Phe Val His Leu Gly His Arg Asp
305                 310                 315                 320 gcc ctc gag gac gac ctc ctc aac cgg aac aac tcc ttc aag ccc ttc     1008
Ala Leu Glu Asp Asp Leu Leu Asn Arg Asn Asn Ser Phe Lys Pro Phe
```

```
                   325                 330                 335
gcc gaa tac aag tcc gac tac gtc tac cag ccc ttc ccc aag acc gtc    1056
Ala Glu Tyr Lys Ser Asp Tyr Val Tyr Gln Pro Phe Pro Lys Thr Val
        340                 345                 350 tgg gag cag atc ctc aac acc tgg ctc gtc aag ccc ggc gcc ggg atc    1104
Trp Glu Gln Ile Leu Asn Thr Trp Leu Val Lys Pro Gly Ala Gly Ile
            355                 360                 365 atg atc ttc gac ccc tac ggc gcc acc atc agc gcc acc ccg gag tcc    1152
Met Ile Phe Asp Pro Tyr Gly Ala Thr Ile Ser Ala Thr Pro Glu Ser
370                 375                 380 gcc acg ccc ttc cct cac cgc aag ggc gtc ctc ttc aac atc cag tac    1200
Ala Thr Pro Phe Pro His Arg Lys Gly Val Leu Phe Asn Ile Gln Tyr
385                 390                 395                 400 gtc aac tac tgg ttc gcc ccg gga gcc gcc gcc gcg ccc ctc tcg tgg    1248
Val Asn Tyr Trp Phe Ala Pro Gly Ala Ala Ala Ala Pro Leu Ser Trp
                405                 410                 415 agc aag gac atc tac aac tac atg gag ccc tac gtg agc aag aac ccc    1296
Ser Lys Asp Ile Tyr Asn Tyr Met Glu Pro Tyr Val Ser Lys Asn Pro
            420                 425                 430 agg cag gcg tac gca aac tac agg gac atc gac ctc ggc agg aac gag    1344
Arg Gln Ala Tyr Ala Asn Tyr Arg Asp Ile Asp Leu Gly Arg Asn Glu
        435                 440                 445 gtg gtc aac gac gtc tcc acc tac gcc agc ggc aag gtc tgg ggc cag    1392
Val Val Asn Asp Val Ser Thr Tyr Ala Ser Gly Lys Val Trp Gly Gln
450                 455                 460 aaa tac ttc aag ggc aac ttc gag agg ctc gcc att acc aag ggc aag    1440
Lys Tyr Phe Lys Gly Asn Phe Glu Arg Leu Ala Ile Thr Lys Gly Lys
465                 470                 475                 480 gtc gat cct acc gac tac ttc agg aac gag cag agc atc ccg ccg ctc    1488
Val Asp Pro Thr Asp Tyr Phe Arg Asn Glu Gln Ser Ile Pro Pro Leu
                485                 490                 495 atc aaa aag tac tga                                                1503
Ile Lys Lys Tyr
            500

<210> SEQ ID NO 6
<211> LENGTH: 500
<212> TYPE: PRT
<213> ORGANISM: Phleum pratense

<400> SEQUENCE: 6

Tyr Phe Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
            20                  25                  30

Pro Ser Val Leu Gly Gln Thr Ile Arg Asn Ser Arg Trp Ser Ser Pro
        35                  40                  45

Asp Asn Val Lys Pro Leu Tyr Ile Ile Thr Pro Thr Asn Val Ser His
50                  55                  60

Ile Gln Ser Ala Val Val Cys Gly Arg Arg His Ser Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Thr Phe Ala Val Val Asp Leu Asn Lys Met Arg Ala Val
            100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile Tyr Lys Ala Ser Pro Thr Leu Ala
```

```
            130                 135                 140
Phe Pro Ala Gly Val Cys Pro Thr Ile Gly Val Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Lys Leu His Asp
                180                 185                 190

Lys Lys Ser Met Gly Asp Asp His Phe Trp Ala Val Arg Gly Gly Gly
                195                 200                 205

Gly Glu Ser Phe Gly Ile Val Val Ala Trp Gln Val Lys Leu Leu Pro
    210                 215                 220

Val Pro Pro Thr Val Thr Ile Phe Lys Ile Ser Lys Thr Val Ser Glu
225                 230                 235                 240

Gly Ala Val Asp Ile Ile Asn Lys Trp Gln Val Val Ala Pro Gln Leu
                245                 250                 255

Pro Ala Asp Leu Met Ile Arg Ile Ile Ala Gln Gly Pro Lys Ala Thr
                260                 265                 270

Phe Glu Ala Met Tyr Leu Gly Thr Cys Lys Thr Leu Thr Pro Leu Met
                275                 280                 285

Ser Ser Lys Phe Pro Glu Leu Gly Met Asn Pro Ser His Cys Asn Glu
    290                 295                 300

Met Ser Trp Ile Gln Ser Ile Pro Phe Val His Leu Gly His Arg Asp
305                 310                 315                 320

Ala Leu Glu Asp Asp Leu Leu Asn Arg Asn Asn Ser Phe Lys Pro Phe
                325                 330                 335

Ala Glu Tyr Lys Ser Asp Tyr Val Tyr Gln Pro Phe Pro Lys Thr Val
                340                 345                 350

Trp Glu Gln Ile Leu Asn Thr Trp Leu Val Lys Pro Gly Ala Gly Ile
                355                 360                 365

Met Ile Phe Asp Pro Tyr Gly Ala Thr Ile Ser Ala Thr Pro Glu Ser
                370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Ala Ala Pro Leu Ser Trp
                405                 410                 415

Ser Lys Asp Ile Tyr Asn Tyr Met Glu Pro Tyr Val Ser Lys Asn Pro
                420                 425                 430

Arg Gln Ala Tyr Ala Asn Tyr Arg Asp Ile Asp Leu Gly Arg Asn Glu
                435                 440                 445

Val Val Asn Asp Val Ser Thr Tyr Ala Ser Gly Lys Val Trp Gly Gln
                450                 455                 460

Lys Tyr Phe Lys Gly Asn Phe Glu Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500

<210> SEQ ID NO 7
<211> LENGTH: 10
<212> TYPE: PRT
<213> ORGANISM: Phleum pratense
<220> FEATURE:
<221> NAME/KEY: MISC_FEATURE
<222> LOCATION: (6)..(6)
```

```
<223> OTHER INFORMATION: undetermined amino acid

<400> SEQUENCE: 7

Ile Val Ala Leu Pro Xaa Gly Met Leu Lys
1               5                   10

<210> SEQ ID NO 8
<211> LENGTH: 14
<212> TYPE: PRT
<213> ORGANISM: Lolium perenne

<400> SEQUENCE: 8

Phe Leu Glu Pro Val Leu Gly Leu Ile Phe Pro Ala Gly Val
1               5                   10

<210> SEQ ID NO 9
<211> LENGTH: 9
<212> TYPE: PRT
<213> ORGANISM: Lolium perenne

<400> SEQUENCE: 9

Gly Leu Ile Glu Phe Pro Ala Gly Val
1               5

<210> SEQ ID NO 10
<211> LENGTH: 12
<212> TYPE: PRT
<213> ORGANISM: Dactylus glomerata

<400> SEQUENCE: 10

Asp Ile Tyr Asn Tyr Met Glu Pro Tyr Val Ser Lys
1               5                   10

<210> SEQ ID NO 11
<211> LENGTH: 11
<212> TYPE: PRT
<213> ORGANISM: Dactylus glomerata

<400> SEQUENCE: 11

Val Asp Pro Thr Asp Tyr Phe Gly Asn Glu Gln
1               5                   10

<210> SEQ ID NO 12
<211> LENGTH: 17
<212> TYPE: PRT
<213> ORGANISM: Dactylus glomerata

<400> SEQUENCE: 12

Ala Arg Thr Ala Trp Val Asp Ser Gly Ala Gln Leu Gly Glu Leu Ser
1               5                   10                  15

Tyr

<210> SEQ ID NO 13
<211> LENGTH: 15
<212> TYPE: PRT
<213> ORGANISM: Dactylus glomerata

<400> SEQUENCE: 13

Gly Val Leu Phe Asn Ile Gln Tyr Val Asn Tyr Trp Phe Ala Pro
1               5                   10                  15

<210> SEQ ID NO 14
<211> LENGTH: 11
<212> TYPE: PRT
```

```
<213> ORGANISM: Cynodon dactylon

<400> SEQUENCE: 14

Lys Thr Val Lys Pro Leu Tyr Ile Ile Thr Pro
1               5                   10

<210> SEQ ID NO 15
<211> LENGTH: 22
<212> TYPE: PRT
<213> ORGANISM: Cynodon dactylon

<400> SEQUENCE: 15

Lys Gln Val Glu Arg Asp Phe Leu Thr Ser Leu Thr Lys Asp Ile Pro
1               5                   10                  15

Gln Leu Tyr Leu Lys Ser
            20

<210> SEQ ID NO 16
<211> LENGTH: 16
<212> TYPE: PRT
<213> ORGANISM: Cynodon dactylon

<400> SEQUENCE: 16

Thr Val Lys Pro Leu Tyr Ile Ile Thr Pro Ile Thr Ala Ala Met Ile
1               5                   10                  15

<210> SEQ ID NO 17
<211> LENGTH: 24
<212> TYPE: PRT
<213> ORGANISM: Cynodon dactylon

<400> SEQUENCE: 17

Leu Arg Lys Tyr Gly Thr Ala Ala Asp Asn Val Ile Asp Ala Lys Val
1               5                   10                  15

Val Asp Ala Gln Gly Arg Leu Leu
            20

<210> SEQ ID NO 18
<211> LENGTH: 14
<212> TYPE: PRT
<213> ORGANISM: Cynodon dactylon

<400> SEQUENCE: 18

Lys Trp Gln Thr Val Ala Pro Ala Leu Pro Asp Pro Asn Met
1               5                   10

<210> SEQ ID NO 19
<211> LENGTH: 15
<212> TYPE: PRT
<213> ORGANISM: Cynodon dactylon

<400> SEQUENCE: 19

Val Thr Trp Ile Glu Ser Val Pro Tyr Ile Pro Met Gly Asp Lys
1               5                   10                  15

<210> SEQ ID NO 20
<211> LENGTH: 19
<212> TYPE: PRT
<213> ORGANISM: Cynodon dactylon
<220> FEATURE:
<221> NAME/KEY: MISC_FEATURE
<222> LOCATION: (8)..(8)
<223> OTHER INFORMATION: undetermined amino acid

<400> SEQUENCE: 20
```

```
Gly Thr Val Arg Gln Leu Leu Xaa Arg Thr Ser Asn Ile Lys Ala Phe
1               5                   10                  15

Gly Lys Tyr

<210> SEQ ID NO 21
<211> LENGTH: 23
<212> TYPE: PRT
<213> ORGANISM: Cynodon dactylon

<400> SEQUENCE: 21

Thr Ser Asn Ile Lys Ala Phe Gly Lys Tyr Lys Ser Asp Tyr Val Leu
1               5                   10                  15

Glu Pro Ile Pro Lys Lys Ser
            20

<210> SEQ ID NO 22
<211> LENGTH: 13
<212> TYPE: PRT
<213> ORGANISM: Cynodon dactylon

<400> SEQUENCE: 22

Tyr Arg Asp Leu Asp Leu Gly Val Asn Gln Val Val Gly
1               5                   10

<210> SEQ ID NO 23
<211> LENGTH: 15
<212> TYPE: PRT
<213> ORGANISM: Cynodon dactylon

<400> SEQUENCE: 23

Ser Ala Thr Pro Pro Thr His Arg Ser Gly Val Leu Phe Asn Ile
1               5                   10                  15

<210> SEQ ID NO 24
<211> LENGTH: 36
<212> TYPE: PRT
<213> ORGANISM: Cynodon dactylon

<400> SEQUENCE: 24

Ala Ala Ala Ala Leu Pro Thr Gln Val Thr Arg Asp Ile Tyr Ala Phe
1               5                   10                  15

Met Thr Pro Tyr Val Ser Lys Asn Pro Arg Gln Ala Tyr Val Asn Tyr
            20                  25                  30

Arg Asp Leu Asp
        35

<210> SEQ ID NO 25
<211> LENGTH: 149
<212> TYPE: DNA
<213> ORGANISM: Phleum pratense

<400> SEQUENCE: 25
caccggaagg gggtgctgtt caacatccag tacgtcaact actggttcgc cccgggagcc      60
ggcgcggcgc cattgtcgtg gagcaaggag atctacaact acatggagcc gtacgtgagc     120
aaggaccccg tccaggccta cgccaacta                                       149

<210> SEQ ID NO 26
<211> LENGTH: 299
<212> TYPE: DNA
<213> ORGANISM: Phleum pratense
```

<400> SEQUENCE: 26

```
actactggtt cgccccggga gccggcgcgg cgccattgtc gtggagcaag gagatctaca    60
actacatgga gccatacgtg agcaagaacc ccaggcaggc ctacgccaac tacagggaca   120
tcgacctcgg gaggaacgag gtggtgaacg acgtctccac cttcagcagc ggtttggtgt   180
ggggccagaa atacttcaag ggcaacttcc agaggctcgc catcaccaag ggcaaggtgg   240
atcccaccga ctacttcagg aacgagcaga gcatcccgcc gctcatcaaa aagtactga   299
```

<210> SEQ ID NO 27
<211> LENGTH: 33
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 27

Tyr Phe Pro Pro Pro Ala Ala Lys Glu Asp Phe Leu Gly Xaa Leu Val
1               5                   10                  15

Lys Glu Ile Pro Pro Arg Leu Leu Tyr Ala Lys Ser Ser Pro Ala Tyr
            20                  25                  30

Pro

<210> SEQ ID NO 28
<211> LENGTH: 18
<212> TYPE: PRT
<213> ORGANISM: Phleum pratense
<220> FEATURE:
<221> NAME/KEY: MISC_FEATURE
<222> LOCATION: (6)..(6)
<223> OTHER INFORMATION: undetermined amino acid

<400> SEQUENCE: 28

Ser Ala Thr Pro Phe Xaa His Arg Lys Gly Val Leu Phe Asn Ile Gln
1               5                   10                  15

Tyr Val

<210> SEQ ID NO 29
<211> LENGTH: 10
<212> TYPE: PRT
<213> ORGANISM: Phleum pratense
<220> FEATURE:
<221> NAME/KEY: MISC_FEATURE
<222> LOCATION: (3)..(8)
<223> OTHER INFORMATION: undetermined amino acid

<400> SEQUENCE: 29

Gly Leu Xaa Tyr Arg Xaa Leu Xaa Pro Glu
1               5                   10

<210> SEQ ID NO 30
<211> LENGTH: 12
<212> TYPE: PRT
<213> ORGANISM: Phleum pratense
<220> FEATURE:
<221> NAME/KEY: MISC_FEATURE
<222> LOCATION: (2)..(9)
<223> OTHER INFORMATION: undetermined amino acid

<400> SEQUENCE: 30

Lys Xaa Met Gly Asp Asp His Phe Xaa Ala Val Arg
1               5                   10

```
<210> SEQ ID NO 31
<211> LENGTH: 9
<212> TYPE: PRT
<213> ORGANISM: Phleum pratense

<400> SEQUENCE: 31

Ala Pro Glu Gly Ala Val Asp Ile Ile
1               5

<210> SEQ ID NO 32
<211> LENGTH: 16
<212> TYPE: PRT
<213> ORGANISM: Phleum pratense

<400> SEQUENCE: 32

Met Glu Pro Tyr Val Ser Ile Asn Pro Val Gln Ala Tyr Ala Asn Tyr
1               5                   10                  15

<210> SEQ ID NO 33
<211> LENGTH: 15
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 33

Tyr Phe Pro Pro Pro Ala Ala Lys Glu Asp Phe Leu Gly Xaa Leu
1               5                   10                  15

<210> SEQ ID NO 34
<211> LENGTH: 10
<212> TYPE: PRT
<213> ORGANISM: Phleum pratense

<400> SEQUENCE: 34

Leu Tyr Ala Lys Ser Ser Pro Ala Tyr Pro
1               5                   10

<210> SEQ ID NO 35
<211> LENGTH: 33
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 35

Tyr Phe Pro Pro Pro Ala Ala Lys Glu Asp Phe Leu Gly Xaa Leu Val
1               5                   10                  15

Lys Glu Ile Pro Pro Arg Leu Leu Tyr Ala Lys Ser Ser Pro Ala Tyr
            20                  25                  30

Pro

<210> SEQ ID NO 36
<211> LENGTH: 29
<212> TYPE: PRT
<213> ORGANISM: Phleum pratense
<220> FEATURE:
<221> NAME/KEY: MISC_FEATURE
<222> LOCATION: (14)..(14)
<223> OTHER INFORMATION: undetermined amino acid

<400> SEQUENCE: 36
```

```
Tyr Phe Pro Pro Pro Ala Ala Lys Glu Asp Phe Leu Gly Xaa Leu Val
1               5                   10                  15

Lys Glu Pro Pro Arg Leu Leu Tyr Ala Lys Ser Ser Pro
            20                  25
```

<210> SEQ ID NO 37
<211> LENGTH: 15
<212> TYPE: PRT
<213> ORGANISM: Phleum pratense
<220> FEATURE:
<221> NAME/KEY: MISC_FEATURE
<222> LOCATION: (4)..(14)
<223> OTHER INFORMATION: undetermined amino acid

<400> SEQUENCE: 37

```
Tyr Phe Pro Xaa Xaa Ala Ala Lys Glu Asp Phe Leu Gly Xaa Leu
1               5                   10                  15
```

<210> SEQ ID NO 38
<211> LENGTH: 15
<212> TYPE: PRT
<213> ORGANISM: Phleum pratense
<220> FEATURE:
<221> NAME/KEY: MISC_FEATURE
<222> LOCATION: (4)..(14)
<223> OTHER INFORMATION: undetermined amino acid

<400> SEQUENCE: 38

```
Tyr Phe Pro Xaa Xaa Ala Lys Lys Glu Asp Phe Leu Gly Xaa Leu
1               5                   10                  15
```

<210> SEQ ID NO 39
<211> LENGTH: 15
<212> TYPE: PRT
<213> ORGANISM: Phleum pratense
<220> FEATURE:
<221> NAME/KEY: MISC_FEATURE
<222> LOCATION: (4)..(14)
<223> OTHER INFORMATION: undetermined amino acid

<400> SEQUENCE: 39

```
Tyr Phe Pro Xaa Xaa Ala Ala Lys Asp Asp Phe Leu Gly Xaa Leu
1               5                   10                  15
```

<210> SEQ ID NO 40
<211> LENGTH: 11
<212> TYPE: PRT
<213> ORGANISM: Phleum pratense
<220> FEATURE:
<221> NAME/KEY: MISC_FEATURE
<222> LOCATION: (4)..(5)
<223> OTHER INFORMATION: undetermined amino acid

<400> SEQUENCE: 40

```
Tyr Phe Pro Xaa Xaa Leu Ala Asn Glu Asp Phe
1               5                   10
```

<210> SEQ ID NO 41
<211> LENGTH: 18
<212> TYPE: PRT
<213> ORGANISM: Phleum pratense
<220> FEATURE:
<221> NAME/KEY: MISC_FEATURE
<222> LOCATION: (6)..(6)
<223> OTHER INFORMATION: undetermined amino acid

<400> SEQUENCE: 41

Ser Ala Thr Pro Phe Xaa His Arg Lys Gly Val Leu Phe Asn Ile Gln
1               5                   10                  15

Tyr Val

<210> SEQ ID NO 42
<211> LENGTH: 10
<212> TYPE: PRT
<213> ORGANISM: Phleum pratense
<220> FEATURE:
<221> NAME/KEY: MISC_FEATURE
<222> LOCATION: (3)..(8)
<223> OTHER INFORMATION: undetermined amino acid

<400> SEQUENCE: 42

Gly Leu Xaa Tyr Arg Xaa Leu Xaa Pro Glu
1               5                   10

<210> SEQ ID NO 43
<211> LENGTH: 12
<212> TYPE: PRT
<213> ORGANISM: Phleum pratense
<220> FEATURE:
<221> NAME/KEY: MISC_FEATURE
<222> LOCATION: (2)..(9)
<223> OTHER INFORMATION: undetermined amino acid

<400> SEQUENCE: 43

Lys Xaa Met Gly Asp Asp His Phe Xaa Ala Val Arg
1               5                   10

<210> SEQ ID NO 44
<211> LENGTH: 9
<212> TYPE: PRT
<213> ORGANISM: Phleum pratense

<400> SEQUENCE: 44

Ala Pro Glu Gly Ala Val Asp Ile Ile
1               5

<210> SEQ ID NO 45
<211> LENGTH: 16
<212> TYPE: PRT
<213> ORGANISM: Phleum pratense

<400> SEQUENCE: 45

Met Glu Pro Tyr Val Ser Ile Asn Pro Val Gln Ala Tyr Ala Asn Tyr
1               5                   10                  15

<210> SEQ ID NO 46
<211> LENGTH: 29
<212> TYPE: DNA
<213> ORGANISM: Phleum pratense
<220> FEATURE:
<221> NAME/KEY: misc_feature
<222> LOCATION: (1)..(29)
<223> OTHER INFORMATION: 'n' means inosin

<400> SEQUENCE: 46
ytntaygcna arwsnwsncc ngcntaycc                                            29

<210> SEQ ID NO 47
<211> LENGTH: 28
<212> TYPE: DNA
<213> ORGANISM: Phleum pratense
<220> FEATURE:
<221> NAME/KEY: misc_feature
<222> LOCATION: (1)..(28)

```
<223> OTHER INFORMATION: 'n' means inosin

<400> SEQUENCE: 47
caymgnaarg gngtnytntt yaayatmc                                               28

<210> SEQ ID NO 48
<211> LENGTH: 26
<212> TYPE: DNA
<213> ORGANISM: Phleum pratense
<220> FEATURE:
<221> NAME/KEY: misc_feature
<222> LOCATION: (1)..(26)
<223> OTHER INFORMATION: 'n' means inosin

<400> SEQUENCE: 48
tarttngcrt angcytgnac nggrtt                                                 26

<210> SEQ ID NO 49
<211> LENGTH: 23
<212> TYPE: DNA
<213> ORGANISM: Phleum pratense

<400> SEQUENCE: 49
actactggtt cgccccggga gcc                                                    23

<210> SEQ ID NO 50
<211> LENGTH: 28
<212> TYPE: DNA
<213> ORGANISM: Phleum pratense

<400> SEQUENCE: 50
tgaagtattt ctggccccac accaaacc                                               28

<210> SEQ ID NO 51
<211> LENGTH: 24
<212> TYPE: DNA
<213> ORGANISM: Phleum pratense

<400> SEQUENCE: 51
cccttggtga tggcgagcct ctgg                                                   24

<210> SEQ ID NO 52
<211> LENGTH: 23
<212> TYPE: DNA
<213> ORGANISM: Phleum pratense

<400> SEQUENCE: 52
ctcagtcctg gggcagacca tcc                                                    23
```

DNA SEQUENCE AND PREPARATION OF GRASS POLLEN ALLERGEN PHL P 4 BY RECOMBINANT METHODS

BACKGROUND OF THE INVENTION

The present invention relates to the provision of the genetic sequence of the major grass pollen allergen Phl p 4. The invention also covers fragments, new combinations of partial sequences and point mutants having a hypoallergenic action. The recombinant DNA molecules and the derived polypeptides, fragments, new combinations of partial sequences and variants can be utilized for the therapy of pollen-allergic diseases. The proteins prepared by recombinant methods can be employed for the in vitro and in vivo diagnosis of pollen allergies.

Type 1 allergies are of importance worldwide. Up to 20% of the population in industrialized countries suffers from complaints such as allergic rhinitis, conjunctivitis or bronchial asthma. These allergies are caused by allergens present in the air (aeroallergens) which are liberated from sources of various origin, such as plant pollen, mites, cats or dogs. Up to 40% of these type 1 allergy sufferers in turn exhibit specific IgE reactivity with grass pollen allergens (Freidhoff et al., 1986, J. Allergy Clin. Immunol. 78, 1190-2001).

The substances which trigger type 1 allergy are proteins, glycoproteins or polypeptides. After uptake via the mucous membranes, these allergens react with the IgE molecules bonded to the surface of mast cells in sensitized individuals. If two IgE molecules are cross linked to one another by an allergen, this results in the release of mediators (for example histamine, prostaglandins) and cytokines by the effector cell and thus in the corresponding clinical symptoms.

A distinction is made between major and minor allergens depending on the relative frequency with which the individual allergen molecules react with the IgE antibodies of allergy sufferers.

In the case of timothy grass (*Phleum pratense*), Phl p 1 (Petersen et al., 1993, J. Allergy Clin. Immunol. 92: 789-796), Phl p 5 (Matthiesen and Lowenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54). Phl p 2/3 (Dolecek et al., 1993, FEBS 335 (3), 299-304), Phl p 4 (Haavik et al., 1985, Int. Arch. Allergy Appl. Immunol. 78: 260-268; Valenta et al., 1992, Int. Arch. Allergy Immunol. 97: 287-294, Fischer et al., 1996, J. Allergy Clin. Immunol. 98: 189-198) and Phl p 13 (Suck et al., 2000, Clin. Exp. Allergy 30: 324-332; Suck et al., 2000, Clin. Exp. Allergy 30: 1395-1402) have hitherto been identified as major allergens.

Phl p 4 has been mentioned as a basic glycoprotein having a molecular weight of between 50 and 60 kDa (Haavik et al., 1985, Int. Arch. Allergy Appl. Immunol. 78: 260-268). The Phl p 4 molecule is trypsin-resistant (Fischer et al., 1996, J. Allergy Clin. Immunol. 98: 189-198), and 70-88% of grass pollen allergy sufferers have IgE antibodies against this molecule (Valenta et al., 1993, Int. Arch. Allergy Immunol. 97: 287-294; Rossi et al., 2001, Allergy 56:1180-1185; Mari, 2003, Clin. Exp. Allergy 33:43-51). Homologous molecules have been described from related grass species (Su et al., 1991, Clin. Exp. Allergy 21: 449-455; Jaggi et al., 1989, Int. Arch. Allergy Appl. Immunol. 89: 342-348; Jaggi et al., 1989, J. Allergy Clin. Immunol. 83: 845-852; Leduc-Brodard et al., 1996, J. Allergy Clin. Immunol. 98:1065-1072; 14-17). These homologous molecules of the *Poaceae* form allergen group 4, whose molecules have high immunological cross-reactivity with one another both with monoclonal mouse antibodies and with human IgE antibodies (Fahlbusch et al., 1993 Clin. Exp. Allergy 23:51-60; Leduc-Brodard et al., 1996, J. Allergy Clin. Immunol. 98:1065-1072; Su et al., 1996, J. Allergy Clin. Immunol. 97:210; Fahlbusch et al., 1998, Clin. Exp. Allergy 28:799-807; Gavrovi-Jankulovi et al., 2000, Invest. Allergol. Clin. Immunol. 10 (6): 361-367; Stumvoll et al. 2002, Biol. Chem. 383: 1383-1396; Grote et al., 2002, Biol. Chem. 383: 1441-1445; Andersson and Lidholm, 2003, Int. Arch. Allergy Immunol. 130: 87-107; Mari, 2003, Clin. Exp. Allergy, 33 (1): 43-51).

In contrast to the above-mentioned major allergens of *Phleum pratense* (Phl p 1, Phl p 2/3, Phl 5a and 5b, Phl p 6 and Phl p 13), the primary structure of Phl p 4 has not yet been elucidated. Likewise, there is no complete sequence of molecules from group 4 from other grass species.

The determination of the N-terminal amino acid sequence was hitherto unsuccessful. However, the causes of this are not known. Fischer et al. (J. Allergy Clin. Immunol., 1996; 98: 189-198) assume N-terminal blocking, but were able to purify an internal peptide after degradation with lysyl endopeptidase and to determine its sequence: IVALPXGMLK (SEQ ID NO: 7).

This peptide has homologies to peptide sequences in the ragweed allergens Amb a1 and Amb a2 and similarities to sequences in proteins from maize (Zm58.2), tomato (lat 59, lat 56) and tobacco (G10) (Fischer et al., 1996, J. Allergy Clin. Immunol. 98: 189-198). For *Lolium perenne*, peptide fragments having the following sequence have been described for the basic group 4 allergen: FLEPVLGLIF-PAGV (SEQ ID NO: 8) and GLIEFPAGV (SEQ ID NO: 9) (Jaggi et al., 1989, Int. Arch. Allergy Appl. Immunol. 89: 342-348).

Peptides have likewise been obtained from the group 4 allergen from *Dactylus glomerata* by enzymatic degradation and sequenced: DIYNYMEPYVSK (P15, SEQ ID NO: 10), VDPTDYFGNEQ (P17, SEQ ID NO: 11), ARTAWVDS-GAQLGELSY (P20, SEQ ID NO: 12) and GVLF-NIQYVNYWFAP (P22, SEQ ID NO: 13) (Leduc-Brodard et al., 1996, J. Allergy Clin. Immunol. 98: 1065-1072).

Peptides have also been obtained from the group 4 allergen of subtropical Bermuda grass (*Cynodon dactylon*) by proteolysis and sequenced: KTVKPLYIITP (S, SEQ ID NO: 14), KQVERDFLTSLTKDIPQLYLKS (V49L, SEQ ID NO: 15), TVKPLYIITPITAAMI (T33S, SEQ ID NO: 16), LRKYGTAADNVIDAKWDAQGRLL (T35L, SEQ ID NO: 17), KWQTVAPALPDPNM (P2, SEQ ID NO: 18), VTWIESVPYIPMGDK (V26L, SEQ ID NO: 19), GTVRDLLXRTSNIKAFGKY (L25L, SEQ ID NO: 20), TSNIKAFGKYKSDYVLEPIPKKS (T22L, SEQ ID NO: 21), YRDLDLGVNQWG (P3, SEQ ID NO: 22), SAT-PPTHRSGVLFNI (V20L, SEQ ID NO: 23), and AAAALPTQVTRDIYAFMTPYVSKNPRQAY-VNYRDLD (V14L, SEQ ID NO: 24) (Liaw et al., 2001, Biochem. Biophys. Research Communication 280: 738-743).

However, these described peptide sequences for Phl p 4 and group 4 allergens have hitherto not resulted in the elucidation of the complete primary structure of group 4 allergens.

The object on which the present invention is based therefore comprised the provision of the complete DNA sequence of Phl p 4 and of a corresponding recombinant DNA on the basis of which the Phl p 4 allergen can be expressed as protein and made available for pharmacologically significant utilization as such or in modified form.

BRIEF DESCRIPTION OF THE DRAWINGS

FIG. 1: Internal DNA sequence (SEQ ID NO: 25) of the Phl p 4 gene Amplicons obtained with genomic DNA were cloned with the degenerated primers No. 30 (sense) and No. 37 (antisense), both shown in italics, and sequenced. The sequence shown represents the consensus from 6 clones. The specific sense primer No. 82 created from this sequence is shown underlined.

FIG. 2: 3' end of the nucleic acid sequence (SEQ ID NO: 26) of the Phl p 4 gene.

Amplicons were obtained with the specific sense primer No. 82 (shown in italics) and an anchor primer in a 3'-RACE PCR with *Phleum pratense* cDNA and sequenced. The sequence shown represents the consensus from 3 sequencing processes and covers the 3' end of the Phl p 4 gene to the stop codon (double underlined). The sequence ranges employed for construction of the antisense primers No. 85 and No. 86 are shown underlined.

FIG. 3: Localization of the Phl p 4 peptides in the deduced amino acid sequence of the Phl p 4 allergen (SEQ ID NO: 2). The peptides P1-P6 (SEQ ID NOs: 27-32) obtained from the amino acid sequencing of the purified and fragmented Phl p 4 allergen can unambiguously be assigned to the amino acid sequence of the Phl p 4 gene derived from the nucleic acid sequence.

FIG. 4: Determination of the identity of recombinant Phl p 4 (rPhl p 4) by means of monoclonal antibodies 5H1 (blot A) and 3C4 (blot B) specific for nPhl p 4 by Western blot. Track 1: *E. coli* total cell extract comprising rPhl p 4 fragment 1-200 Track 2: *E. coli* total cell extract comprising rPhl p 4 fragment 185-500 Track 3: *E. coli* total cell extract comprising rPhl p 4 Track 4: purified nPhl p 4 from *Phleum pratense* (←): termination or degradation fragments of C-terminal rPhl p 4 fragment or rPhl p 4 entire molecule.

FIG. 5: Determination of the reactivity of recombinant Phl p 4 (rPhl p 4) using IgE from sera of grass pollen allergy sufferers by Western blot. Extracts of transformed *E. coli* cells which either express the complete Phi p 4 gene or the N-terminal fragment 1-200 or the C-terminal fragment 185-500 were separated in the SDS-PAGE and transferred to nitrocellulose membranes. The blot was incubated with sera from grass pollen-allergic donor A, B or C, and bound IgE was subsequently detected calorimetrically via an anti-human IgE antibody conjugated with alkaline phosphatase. Track 1: *E. coli* total cell extract comprising rPhl p 4 fragment 1-200 Track 2: *E. coli* total cell extract comprising rPhl p 4 fragment 185-500 Track 3: *E. coli* total cell extract comprising rPhl p 4 Track 4: purified nPhl p 4 from *Phleum pretense*.

The numbers used above and below for nucleotide or amino acid sequences "SEQ ID NO" relate to the sequence protocol attached to the description.

DESCRIPTION OF THE INVENTION

The present invention now provides for the first time the genetic sequence of the major grass pollen allergen Phl p 4, with three dominant sequences (SEQ ID NOS: 1, 3 and 5) arising from the single nucleotide polymorphisms (SNPs) found.

The present invention therefore relates to a DNA molecule corresponding to a nucleotide sequence selected from a group consisting of SEQ ID NO: 1, SEQ ID NO: 3 and SEQ ID NO: 5 or a DNA molecule corresponding to a nucleotide sequence which encodes for the major allergen Phl p 4 from *Phleum pratense*.

The invention also covers fragments, new combinations of partial sequences and point mutants having a hypoallergenic action.

The invention therefore furthermore relates to corresponding partial sequences, a combination of partial sequences or exchange, elimination or addition mutants which encode for an immunomodulatory, T-cell-reactive fragment of a group 4 allergen of the *Poaceae*.

In addition to the group 4 allergens of the other grass species, the group 13 allergens are also of interest in connection with the present invention since they exhibit a very similar molecular weight to the group 4 allergens in the SDS-PAGE and are difficult to separate by biochemical techniques (Suck et al., 2000, Clin. Exp. Allergy 30: 324-332, Suck et al., 2000, Clin. Exp. Allergy 30: 1395-1402). With the aid of the protein and DNA sequence according to the invention which is now available for the first time, however, it can unambiguously be shown that groups 4 and 13 have significantly different amino acid sequences.

With knowledge of the DNA sequence of naturally occurring allergens, it is now possible to prepare these allergens as recombinant proteins which can be used in the diagnosis and therapy of allergic diseases (Scheiner and Kraft, 1995, Allergy 50: 384-391).

A classical approach to effective therapeutic treatment of allergies is specific immunotherapy or hypo-sensitization (Fiebig, 1995, Allergo J. 4 (6): 336-339, Bousquet et al., 1998, J. Allergy Clin. Immunol. 102(4): 558-562). In this method, the patient is injected subcutaneously with natural allergen extracts in increasing doses. However, there is a risk in this method of allergic reactions or even anaphylactic shock. In order to minimize these risks, innovative preparations in the form of allergoids are being employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimization would be possible with allergens prepared by recombinant methods. Defined cocktails of high-purity allergens prepared by recombinant methods, optionally matched to the individual sensitization patterns of the patients, could replace extracts from natural allergen sources since these, in addition to the various allergens, contain a relatively large number of immunogenic, but non-allergenic secondary proteins.

Realistic perspectives which may result in reliable hyposensitization with expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed TH-cell equilibrium in allergy sufferers is immunotherapeutic DNA vaccination. This involves treatment with expressible DNA which encodes for the relevant allergens. Initial experimental evidence of allergen-specific influencing of the immune response has been furnished in rodents by injection of allergen-encoding DNA (Hsu et al., 1996, Nature Medicine 2 (5): 540-544).

The present invention therefore also relates to a DNA molecule described above or below or a corresponding recombinant expression vector as medicament.

The corresponding proteins prepared by recombinant methods can be employed for the therapy and for the in vitro and in vivo diagnosis of pollen allergies.

For preparation of the recombinant allergen, the cloned nucleic acid is ligated to an expression vector, and this construct is expressed in a suitable host organism. After biochemical purification, this recombinant allergen is available for the detection of IgE antibodies by established methods.

The present invention therefore furthermore relates to a recombinant expression vector comprising a DNA molecule described above or below, functionally linked to an expression control sequence and a host organism transformed with the said DNA molecule or the said expression vector.

The invention likewise relates to the use of at least one DNA molecule described above or at least one expression vector described above for the preparation of a medicament for immunotherapeutic DNA vaccination of patients having allergies in the triggering of which group 4 allergens of the *Poaceae* are involved and/or for the prevention of such allergies.

As already stated, the invention can be used as an essential component in a recombinant allergen- or nucleic acid-containing preparation for specific immunotherapy. There are a number of possibilities here. Firstly, the protein with an unchanged primary structure may be a constituent of the preparation. Secondly, through specific deletion of IgE epitopes of the entire molecule or the preparation of individual fragments which encode for T-cell epitopes, a hypoallergenic (allergoidal) form can be used in accordance with the invention for therapy in order to prevent undesired side effects. Finally, the nucleic acid per se, if ligated with a eukaryotic expression vector, gives a preparation which on direct application modifies the allergic immune state in the therapeutic sense.

The invention thus relates to recombinant DNA molecules corresponding to SEQ ID NOS: 1, 3 or 5, where the nucleotide sequence of positions 1-69 has been derived from the amino acid sequence of the Phl p 4 N-terminus. Codons which frequently occur in *E. coli* were used here. From position 70, the DNA sequence corresponds to that which has been identified in genomic and cDNA of *Phleum pratense*.

The present invention therefore furthermore relates to a DNA molecule comprising a nucleotide sequence according to SEQ ID NO: 1, SEQ ID NO: 3 or SEQ ID NO: 5, commencing with position 70, which encodes for a polypeptide having the properties of the major allergen Phl p 4 from *Phleum pratense*.

Furthermore, the present invention relates to the polypeptides encoded by one or more of the above-described DNA molecules, preferably in their property as medicament.

These are, in particular, polypeptides according to SEQ ID NO: 2, SEQ ID NO: 4 or SEQ ID NO: 6, where amino acid positions 1-33 have been determined by N-terminal amino acid sequencing of the isolated natural Phl p 4 allergen. Positions 24-500 were derived from the DNA sequence according to SEQ ID NOS: 1, 3 and 5. Variable amino acids at positions 6, 7, 8 and 9 originate from the N-terminal protein sequencing of various preparations of natural Phl p 4 (Table 1).

Accordingly, the invention also relates to a process for the preparation of polypeptides of this type by cultivation of a host organism according to claim 11 and isolation of the corresponding polypeptide from the culture.

The invention likewise relates to the use of at least one polypeptide described above for the preparation of a medicament for the diagnosis and/or treatment of allergies in the triggering of which group 4 allergens of the *Poaceae* are involved and for the prevention of such allergies.

These polypeptides or proteins according to the invention which act as allergens for humans are present in the pollen grains of *Phleum pratense*. The pollen grains of the other *Poaceae* species, such as, for example, *Lolium perenne, Dactylis glomerata, Poa pratensis, Cynodon dactylon, Holcus lanatus*, inter alia, contain homologous allergen molecules (group 4 allergens).

The homology of these molecules has been demonstrated through their immunological cross-reactivity both with murine monoclonal antibodies and also with human IgE antibodies.

Consequently, the invention also relates to sequences which are homologous to the Phl p 4 DNA sequence and corresponding DNA molecules of group 4 allergens from other *Poaceae* such as, for example, *Lolium perenne, Dactylis glomerata, Poa pratensis, Cynodon dactylon, Holcus lanatus, Triticum aestivum* and *Hordeum vulgare*, which, owing to the sequence homology which exists, hybridize with Phl p 4 DNA under stringent conditions or have immunological cross-reactivity with respect to Phl p 4.

The following procedure was followed in the determination of the protein and DNA sequence of Phl p 4:

The natural allergen Phl p 4 was purified and isolated by described methods (Fahlbusch et al. 1998, Clin. Exp. Allergy 28: 799-807, Suck et al. 2000, Clin. Exp. Allergy 30: 1395-1402). The micropurification and the removal of traces of the group 13 allergen was carried out by the method described by Suck et al. (2000, Clin. Exp. Allergy 30: 1395-1402).

The N-terminal amino acid sequence of this Phl p 4 isolated from *Phleum pretense* was determined by means of Edman degradation. The N-terminal sequences (P1a-f shown in Table 1 were determined with various batches of Phl p 4. The consensus sequence for the first 15 positions is regarded as being the following sequence: YFPP'P'AAKED-FLGXL (SEQ ID NO: 33). Position 14 could not be determined; it is probably occupied by cysteine. The different amino acids in positions 6, 7, 8 and 9 in the different batches indicate variations in the sense of isoforms. Positions 4 and 5 are occupied by hydroxyproline (P'), which was unambiguously determined by specific analysis in the analyses of preparations p1-a and -b.

Treatment of the SDS-denatured Phl p 4 with the endopeptidase Glu-C (Promega, Heidelberg, Germany) gave various peptides. The amino acid sequences shown in Table 1 were determined for two peptides (P2 and P3). 2 peptides (P4 and P5) were purified by cleavage using the endopeptidase Lys-C (Roche, Mannheim, Germany) and sequenced (Table 1). A further peptide (P6) was isolated by CNBr cleavage and the amino acid sequence was determined (Table 1).

The amino acid sequences of the N-terminal sequence and the internal peptides 2 and 6 were used as the basis for the construction of degenerated primers. Amplicons were prepared with the sense primer No. 30 and the antisense primer No. 37 (Table 2) using genomic DNA from *Phleum pratense*. The clones obtained from these amplicons were sequenced (FIG. 1) and used for the construction of the specific sense primer No. 82 (Table 2). Using a cDNA prepared from the representative mRNA population from *Phleum pretense* pollen and the specific sense primer No. 82 according to the invention and the anchor primer AUAP (Life Technologies, Karlsruhe, Germany), a PCR was carried out under stringent conditions. This approximately 450 kb amplicon was sequenced and the missing sequence as far as the 3' end of the Phl p 4 gene was thus identified (FIG. 2). Based on this C-terminal Phl p 4 sequence determined in accordance with the invention, the specific antisense primers No. 85 and No. 86 were constructed (Table 2). Based on the N-terminal amino acid sequence of the Phl p 4 peptide P1-a (Table 1), the degenerated sense primer No. 29, derived from the DNA encoding for amino acid positions 24-33 (LYAKSSPAYP (SEQ ID NO: 34)), was constructed.

A PCR was carried out with primers No. 29 and No. 86 using genomic *Phleum pratense* DNA. This PCR product was employed as the basis for a second PCR (nested PCR) with primers No. 29 and No. 85. The amplicons were inserted into the vector pGEM T-easy (Promega, Heidelberg, Germany), cloned and sequenced. This sequence begins at position 24 calculated from the N-terminus or position 70 of the DNA sequence in accordance with SEQ ID NOS: 1, 3 or 5 and extends to primer No. 85 (position 1402 in SEQ ID NOS: 1, 3 or 5), which is localized in the already determined C-terminal section of the Phl p 4 gene. Using these data, the complete amino acid sequence of the Phl p 4 molecule can be constructed from the first 33 amino acid positions, determined by protein sequencing, and the deduced amino acid sequence (477 positions), which can be derived from the clones prepared with primers No. 29/No. 85 and No. 82/anchor primer. The two clones overlap in 197 positions of their nucleotide sequence. The peptide encoded by clone No. 29/No. 85 overlaps in 10 amino acid positions with the N-terminal sequence (positions 1-33), determined by direct amino acid sequencing, of Phl p 4, where the amino acids determined by the two methods correspond.

The amino acid sequence of Phl p 4 based on the directly determined N-terminal amino acids and the deduced amino acid sequence corresponds to the sequences listed in the sequence protocol under SEQ ID NOS: 2, 4 and 6.

PCR products were prepared with the specific sense primer No. 88 (Table 2) and the specific antisense primer No. 86 both using genomic and using cDNA from *Phleum pratense* and sequenced directly.

This enables PCR errors to be excluded and genetic variations (single nucleotide polymorphisms) to be discovered.

The single nucleotide polymorphisms found for the DNA sequence SEQ ID NO: 1 are shown in Table 3. Some of these single nucleotide polymorphisms result in modified amino acids. These are shown in Table 4. Furthermore, DNA clones which result in deviating amino acids with respect to the dominant sequences SEQ ID NOS: 2, 4 and 6 were sequenced (Table 5). These amino acid variations are to be regarded as isoforms of the Phl p 4 molecule. The existence of such isoforms is to be expected owing to the heterogeneous isoelectric behavior of natural Phl p 4. All pollen allergens known hitherto have such isoforms. The fact that the DNA fragment determined with primers No. 29 and 86 actually encodes for a protein which is identical with the natural Phl p 4 allergen can also be demonstrated, inter alia, by the fact that homologous peptide sequences in the deduced amino acid sequence of the recombinant Phl p 4 molecule according to the invention are found (FIG. 3) for the identified internal peptides P3, P4 and P5 (Table 1) of natural Phl p 4. The Phl p 4 amino acid sequence described shows that it is a basic molecule having a calculated isoelectric point of 8.99 (SEQ ID NO: 2), 8.80 (SEQ ID NO: 4) or 9.17 (SEQ ID NO: 6), consisting of 500 amino acids. The quantitative amino acid composition is shown in Table 6. The calculated molecular weight of recombinant Phl p 4 is 55.762 (SEQ ID NO: 2), 55.734 (SEQ ID NO: 4) or 55.624 (SEQ ID NO: 6) daltons. This calculated molecular weight agrees very well with the molecular weight of natural Phl p 4 of 55 kDa determined by SDS-PAGE (Fahlbusch et al., 1998, Clin. Exp. Allergy 28: 799-807 and Suck et al., 2000, Clin. Exp. Allergy 30: 1395-1402).

Molecular weights of between 50 and 60 kDa have also been described for the group 4 allergens of related grass species (Su et al., 1991, Clin. Exp. Allergy 21: 449-455; Jaggi et al., 1989, Int. Arch. Allergy Appl. Immunol. 89: 342-348; Jaggi et al., 1989, J. Allergy Clin. Immunol. 83: 845-852; Leduc-Brodard et al., 1996, J. Allergy Clin. Immunol. 98: 1065-1072; 14-17).

For the preparation of the recombinant Phl p 4 protein, the DNA sequence according to SEQ ID NOS: 1, 3 and/or 5 encoding for Phl p 4 was inserted into expression vectors (for example PPROEX, pλCro, pSE 380). For the N-terminal amino acids known from protein sequencing, *E. coli* optimized codons were used.

After transformation into *E. coli*, expression and purification of the recombinant Phl p 4 by various separation methods, the resultant protein was subjected to a refolding process.

This rPhl p 4 protein obtained in this way gives a single band in the SDS-PAGE which covers the same molecular weight range as natural Phl p 4. The immunological reactivity of rPhl p 4 has been demonstrated by reaction with the murine monoclonal antibodies 5H1 and 3C4, which had been induced using natural Phl p 4 and cross-react with the homologous proteins (group 4) of the *Poaceae* (Fahlbusch et al., 1998, Clin. Exp. Allergy 28:799-807; Gavrovi-Jankulovi et al., 2000, Invest. Allergol. Clin. Immunol. 10 (6): 361-367) (FIG. 4). rPhl p 4 reacts with IgE antibodies of allergy sufferers which have demonstrated IgE reactivity with natural Phl p 4. This IgE reactivity and thus the action as allergen have been demonstrated both in the dot test, Western blot and also after adsorption of the allergen on polystyrene microtitre plates. Detection by Western blot is shown in FIG. 5. On reaction of rPhl p 4 with basophiles of allergen group 4-reactive grass pollen allergy sufferers, these are stimulated to increased expression of the activation marker CD 203c. This basophile activation by rPhl p 4 clearly shows that this molecule also acts functionally as an allergen.

This rPhl p 4 allergen can thus be employed for the highly specific diagnosis of grass pollen allergy sufferers. This diagnosis can be carried out in vitro by detection of specific antibodies (IgE, IgG1-4, IgA) and reaction with IgE-loaded effector cells (for example basophiles from the blood) or in vivo by skin test reactions and provocation at the reaction organ.

The reaction of rPhl p 4 with T-lymphocytes of grass pollen allergy sufferers has been detected by allergen-specific stimulation of the T-lymphocytes for proliferation and cytokine synthesis both with T-cells in freshly prepared blood lymphocytes and on established nPhl p 4-reactive T-cell lines and clones.

Based on the rPhl p 4 DNA sequence described, partial sequences encoding for peptides having from 50 to 350 amino acids were cloned into expression vectors. These partial sequences cover sequentially the complete sequence of rPhl p 4, with overlaps of at least 12 amino acids occurring. The expressed peptides correspond to Phl p 4 fragments. These Phl p 4 fragments do not react individually or as a mixture with the IgE antibodies of allergy sufferers or only do so to a small extent, so that they can be classified as hypoallergenic. In contrast, the mixture of these fragments is capable, in the same way as complete recombinant or natural Phl p 4, of stimulating T-lymphocytes of grass pollen allergy sufferers having Phl p 4 reactivity.

FIG. 4 shows as an example the characterization of two such Phl p 4 fragments corresponding to amino acids 1-200 and 185-500 by binding to Phl p 4-specific monoclonal mouse antibodies. The C-terminal fragment 185-500 reacts only with monoclonal antibody 5H1, while the N-terminal fragment 1-200 clearly reacts with monoclonal antibody 3C4. It can be seen from FIG. 5 that fragment 185-500 reacts less strongly with the IgE from the sera of allergy sufferers B and C, i.e. is less allergenic than fragment 1-200, which has reduced IgE reactivity (hypoallergeneity), at least to patient serum C.

The present invention therefore also relates to a DNA molecule described above or below, encoding for a fragment 1-200, with amino acids 1-200 of Phl p 4, and a DNA molecule encoding for a fragment 285-500, with amino acids 285-500 of Phl p 4.

The triplets encoding for the cysteines were modified by site-specific mutagenesis in such a way that they encode for other amino acids, preferably serine. Both variants in which individual cysteines have been replaced and those in which various combinations of 2 cysteine radicals or all 5 cysteines have been modified have been prepared. The expressed proteins of these cysteine point mutants have highly reduced or zero reactivity with IgE antibodies of allergy sufferers, but react with the T-lymphocytes of these patients. The present invention therefore furthermore relates to a DNA molecule described above or below in which one, more or all of the cysteine radicals of the corresponding polypeptide have been replaced by another amino acid by site-specific mutagenesis.

The immunomodulatory activity of the hypoallergenic fragments which correspond to polypeptides having T-cell epitopes and those of the hypoallergenic point mutants (for example cysteine polymorphisms) has been demonstrated by reaction thereof with T-cells of grass pollen allergy sufferers.

Such hypoallergenic fragments or point mutants of the cysteines can be employed as preparations for the hypo sensitization of allergy sufferers since they react with equal effectiveness with the T-cells, but, owing to the reduced or entirely absent IgE reactivity, result in reduced IgE-mediated side effects.

If the nucleic acids encoding for the hypoallergenic Phl p 4 variants or the unmodified DNA encoding for Phl p 4 are ligated with a human expression vector, these constructs can likewise be used as preparations for immuno-therapy (DNA vaccination).

Finally, the present invention relates to pharmaceutical compositions comprising at least one DNA molecule described above or at least one expression vector described above and optionally further active ingredients and/or adjuvants for immunotherapeutic DNA vaccination of patients having allergies in the triggering of which group 4 allergens of the *Poaceae* are involved and/or for the prevention of such allergies.

A further group of pharmaceutical compositions according to the invention comprises, instead of the DNA, at least one polypeptide described above and is suitable for the diagnosis and/or treatment of the said allergies.

Pharmaceutical compositions in the sense of the present invention comprise, as active ingredients, a polypeptide according to the invention or an expression vector and/or respective pharmaceutically usable derivatives thereof, including mixtures thereof in all ratios. The active ingredients according to the invention can be brought here into a suitable dosage form together with at least one solid, liquid and/or semi-liquid excipient or adjuvant and optionally in combination with one or more further active ingredients.

Particularly suitable adjuvants are immunostimulatory DNA or oligonucleotides having CpG motives.

These compositions can be used as therapeutic agents or diagnostic agents in human or veterinary medicine. Suitable excipients are organic or inorganic substances which are suitable for parenteral administration and do not adversely affect the action of the active ingredient according to the invention. Particularly suitable for parenteral administration are solutions, preferably oil-based or aqueous solutions, furthermore suspensions, emulsions or implants. The active ingredient according to the invention may also be lyophilized and the resultant lyophilisates used, for example, for the preparation of injection preparations. The compositions indicated may be sterilized and/or comprise adjuvants, such as lubricants, preservatives, stabilizers and/or wetting agents, emulsifiers, salts for modifying the osmotic pressure, buffer substances and/or a plurality of further active ingredients.

Furthermore, sustained-release preparations can be obtained by corresponding formulation of the active ingredient according to the invention.

The invention thus also serves for improving in vitro diagnosis as part of allergen component-triggering identification of the patient-specific sensitization spectrum. The invention likewise serves for the preparation of significantly improved preparations for the specific immunotherapy of grass pollen allergies.

TABLE 1

Amino acid sequence of Phl p4 peptides

| Preperation | Peptide batch | SEQ ID NO | Amino acids 1 | 6 | 11 | 16 | 21 | 26 | 31 |
|---|---|---|---|---|---|---|---|---|---|
| Intact Phl p4 | P1-a | 35 | YPPP'P' | AAKED | FLGXL | VKEIP | PRLLY | AKSSP | AVP |
| | P1-b | 36 | YPPP'P' | AAKED | FLGXL | VKE-P | PRLLY | AKSSP | |
| | P1-c | 37 | YRPXX | AAKED | FLGXL | | | | |
| | P1-d | 38 | YPPXX | AKEED | FLGXL | | | | |
| | P1-e | 39 | YFPXX | AAKDD | FLGXL | | | | |
| | P1-f | 40 | YPPXX | LAMED | F | | | | |
| Glu-C fragments | P2 | 41 | SATPF | KHREG | VLFNI | QTV | | | |
| | P3 | 42 | GLXYR | XLXPE | | | | | |
| Lys-C fragments | P4 | 43 | KXMGD | DNFXA | VR | | | | |
| | P5 | 44 | APEGA | VDI I | | | | | |
| CNBr fragment | P6 | 45 | MEPYV | SINPV | QAYAE | Y | | | |

TABLE 2

Degenerated and specific sense and antisense primers constructed on the basis of Phl p 4 peptide sequences and DNA sequences

| Primer No. | Peptide/ DNA | Sense/ anti- sense | SEQ ID NO | Nucleotide sequence |
|---|---|---|---|---|
| 29 | Phl p 4-P1 | s | 46 | YTN TAY GCN AAR WSN WSN CCN GCN TAY CC |
| 30 | Phl P 4-P2 | s | 47 | CAY WGN AAR GGN GTN YTN TTY AAY ATN C |
| 37 | Phl p 4-P6 | as | 48 | TAR TTN GCH TAN GCT TGN ACN GGR TT |
| 82 | Phl p 4-DNA-NYW | s | 49 | ACT ACT GGT TCG CCC CGG GAG CC |
| 85 | Phl p 4-DNA-GLV | as | 50 | TGA AGT ATT TCT GGC CCT ACA CCA AAC C |
| 86 | Phl p 4-DNA-QRL | as | 51 | CCC TTG GTG ATG GCG AGC CTC TGG |
| 88 | Phl p 4-DNA-PSV | s | 52 | CTC AGT CCT GGG GCA GAC CAT CC |

The nucleotide sequences of primers 82, 85, 86 and 88 is shown in the usual 4-letter code. In the case of primers 29, 30 and 37, the IUPAC-IUB DNA code is used; the letter 'N' here stands for inosine.

TABLE 3

Detected single nucleotide polymorphisms

| Position in sequence | Nucleotide according to SEQ ID NO 1 | Detected SNPs |
|---|---|---|
| 85 | T | A |
| 130 | C | A |
| 159 | G | A |
| 160 | A | C |
| 169 | G | A |
| 185 | C | T |
| 186 | C | A |
| 222 | G | C |
| 226 | G | A |
| 227 | G | C |
| 228 | T | C |
| 237 | C | T |
| 273 | C | T |
| 285 | C | T |
| 286 | C | T |
| 298 | G | A |
| 299 | A | C |
| 303 | C | T |
| 309 | C | G |
| 318 | T | C |
| 320 | G | A |
| 333 | C | G |
| 348 | G | C |
| 369 | C | G |
| 409 | C | T |
| 411 | C | T |
| 420 | T | C |
| 421 | A | C |
| 423 | A | C |
| 424 | G | A |
| 425 | T | C |
| 456 | C | G |
| 462 | C | A |
| 522 | G | C |
| 525 | C | G |
| 567 | G | A |
| 618 | C | T |
| 655 | A | C |
| 657 | G | A |
| 662 | G | A |
| 680 | C | T |
| 684 | G | C |
| 690 | C | A |
| 691 | G | A |
| 693 | G | A |
| 703 | C | T, A |
| 710 | A | C |
| 711 | G | A |
| 713 | C | T |
| 743 | G | A |
| 750 | G | A |
| 768 | C | T |
| 773 | A | C |
| 790 | G | A |
| 798 | G | C |
| 801 | G | A |
| 804 | C | G |
| 809 | C | A |
| 834 | G | C |
| 844 | C | A |
| 859 | A | T |
| 865 | A | G |
| 879 | G | C |
| 895 | G | C |
| 900 | G | C, A |
| 918 | G | A |
| 961 | A | G |
| 962 | A | C |
| 964 | A | C |
| 987 | G | C |
| 994 | A | T |
| 1020 | G | A |
| 1023 | G | C |
| 1036 | G | C |
| 1040 | C | T |
| 1041 | G | C |

TABLE 3-continued

Detected single nucleotide polymorphisms

| Position in sequence | Nucleotide according to SEQ ID NO 1 | Detected SNPs |
|---|---|---|
| 1047 | C | A |
| 1051 | A | G |
| 1052 | G | A, C |
| 1053 | G | A, C, T |
| 1056 | G | C |
| 1069 | T | C |
| 1073 | G | A |
| 1084 | C | G |
| 1086 | G | C |
| 1090 | C | T |
| 1098 | G | C |
| 1151 | G | C |
| 1152 | G | C |
| 1155 | G | C |
| 1161 | G | C |
| 1185 | C | G |
| 1229 | G | C |
| 1233 | G | C |
| 1239 | A | C |
| 1240 | T | C |
| 1242 | G | C |
| 1257 | G | C |
| 1266 | C | T |
| 1269 | C | T |
| 1278 | A | C, G |
| 1305 | C | G |
| 1308 | C | T |
| 1311 | C | A |
| 1335 | G | C |
| 1350 | G | C |
| 1357 | T | A |
| 1359 | A | G |
| 1370 | G | C |
| 1377 | T | C |
| 1378 | T | A |
| 1379 | T | A |
| 1383 | G | C |
| 1398 | C | T |
| 1411 | T | C |
| 1414 | C | G |
| 1425 | C | A |
| 1428 | C | T |
| 1443 | G | C |
| 1449 | C | T |
| 1464 | G | A |
| 1485 | G | A |
| 1498 | A | C |

TABLE 4

Amino acid exchanges as a consequence of single nucleotide polymorphisms

| Position in sequence | Amino acid according to SEQ ID NO 2 | Detected exchanges |
|---|---|---|
| 6 | A | L |
| 7 | A | K |
| 8 | K | N |
| 9 | E | D |
| 29 | S | T |
| 54 | I | L |
| 57 | V | I |
| 62 | A | V |
| 76 | G | T, N, S |
| 100 | E | T |
| 107 | S | N |
| 137 | H | Y |
| 141 | T | P |
| 142 | V | A, T |
| 189 | T | K |
| 219 | K | Q |
| 221 | R | K |
| 227 | P | L |

TABLE 4-continued

Amino acid exchanges as a consequence of single nucleotide polymorphisms

| Position in sequence | Amino acid according to SEQ ID NO 2 | Detected exchanges |
|---|---|---|
| 231 | V | I |
| 235 | P | T, S |
| 237 | K | T |
| 238 | A | V |
| 248 | R | K |
| 258 | D | A |
| 264 | V | I |
| 270 | T | K |
| 282 | Q | K |
| 287 | M | L |
| 289 | S | G |
| 299 | A | P |
| 321 | N | A |
| 322 | I | L |
| 332 | T | S |
| 346 | E | Q |
| 347 | P | L |
| 351 | R | E, T |
| 357 | F | L |
| 358 | S | N |
| 362 | L | V |
| 364 | P | S |
| 384 | W | S |
| 410 | G | A |
| 419 | E | D |
| 456 | F | Y |
| 457 | S | A, N |
| 460 | L | K |
| 468 | K | M |
| 472 | Q | E |
| 498 | K | Q |

TABLE 5

Deviating amino acid positions in individual recombinant Phl p 4 clones compared with SEQ ID NO 2

| Example | Deviating positions* |
|---|---|
| Clone 1 | L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, S384, A410, D419, Y456, A457, K460, E472 |
| Clone 2 | L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, E472 |
| Clone 3 | P141, K282, L287, P299, L347, E351 |
| Clone 4 | G289, A410, D419, Y456, A457, K460, E472 |
| Clone 5 | L347, E351, S384, A410, D419, Y456, A457, K460, E472 |
| Clone 6 | N107, Y137, P141, T142, K189, Q219, K221, I231, S235, T237, V238, K248, A258, I264, K270, K281, L287, P299, A321, L322, S332, Q346, P347, T351, L357, N358, V362, S384, A410, D419, Y456, A457, K460 |
| Clone 7 | K248, A258, I264, K270, K282, L287, P299, A321, L322, S332, Q346, P347, T351, L357, N358, V362, S384 |
| Clone 8 | Q219, K221, I231, S235, T237, V238, K248, A258, I264, K270, K282, L287, P299, E351 |
| Clone 9 | M231, T246, A251, C263, G289, L307, L309, E334 |
| Clone 10 | Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, E472 |
| Clone 11 | Insertion of GA between positions 407 and 408 |

*[Amino acid according to SEQ ID NO 2/position in sequence/deviating amino acid]

TABLE 6

Amino acid composition of Phl 4

| Amino acids | Number | % by weight |
|---|---|---|
| Charged | 138/138/138 | 33.89/33.86/33.93 |
| Acid | 45/46/43 | 9.82/10.05/9.38 |
| Basic | 54/53/55 | 13.67/13.39/13.78 |
| Polar | 120/119/174 | 24.88/24.71/25.89 |
| Hydrophobic | 180/180/180 | 35.64/35.66/35.43 |
| A Ala | 40/40/41 | 5.10/5.10/5.24 |
| C Cys | 5/5/5 | 0.92/0.93/0.93 |
| D Asp | 24/24/24 | 4.95/4.96/4.97 |
| E Glu | 21/22/19 | 4.86/5.10/4.41 |
| F Phe | 24/24/22 | 6.33/6.34/5.82 |
| G Gly | 42/42/40 | 4.30/4.30/4.10 |
| H His | 10/10/9 | 2.46/2.46/2.22 |
| I Ile | 29/29/30 | 5.88/5.89/6.10 |
| K Lys | 29/29/33 | 6.67/6.67/7.60 |
| L Leu | 33/33/35 | 6.70/6.70/7.12 |

TABLE 6-continued

Amino acid composition of Phl 4

| Amino acids | Number | % by weight |
|---|---|---|
| M Met | 11/11/10 | 2.59/2.59/2.36 |
| N Asn | 22/22/23 | 4.50/4.50/4.72 |
| P Pro* | 38/39/39 | 6.62/6.80/6.81 |
| Q Glu | 15/15/15 | 3.45/3.45/3.46 |
| R Arg | 25/24/22 | 7.00/6.73/6.18 |
| S Ser | 32/32/33 | 5.00/5.00/5.17 |
| T Thr | 22/21/22 | 3.99/3.81/4.00 |
| V Val | 41/41/40 | 7.29/7.29/7.13 |
| W Trp | 13/13/12 | 4.34/4.34/4.02 |
| Y Tyr | 24/24/26 | 7.02/7.03/7.63 |

*including hydroxyproline

The values are given for the three dominant sequences in the order SEQ ID NO2/SEQ ID NO: 4/SEQ ID NO: 6.

---

The invention claimed is:

1. A method for the treatment of allergies in the triggering of which group 4 allergens of the *Poaceae* are involved in a subject in need thereof, comprising administering to said subject an effective amount of the polypeptide encoded by a DNA sequence selected from the group consisting of
   (a) a DNA molecule encoding the polypeptide sequence of SEQ ID NO: 2, SEQ ID NO: 4 or SEQ ID NO: 6;
   (b) SEQ ID NO 1, SEQ ID NO 3 and SEQ ID NO 5; and
   (c) a DNA molecule encoding a polypeptide variant consisting of the polypeptide sequence of SEQ ID NO: 2 with the amino acid variations set forth in clones 1 to 11, wherein
      (1) clone 1 consists of L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, S384, A410, D419, Y456, A457, K460, and E472;
      (2) clone 2 consists of L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, and E472;
      (3) clone 3 consists of P141, K282, L287, P299, L347, and E351;
      (4) clone 4 consists of G289, A410, D419, Y456, A457, K460, and E472;
      (5) clone 5 consists of L347, E351, S384, A410, D419, Y456, A457, K460, and E472;

(6) clone 6 consists of N107, Y137, P141, T142, K189, Q219, K221, I231, S235, T237, V238, K248, A258, 1264, K270, K282, L287, P299, A321, L322, S332, Q346, P347, T351, L357, N358, V362, S384, A410, D419, Y456, A457, and K460;

(7) clone 7 consists of K248, A258, 1264, K270, K282, L287, P299, A321, L322, S332, Q346, P347, T351, L357, N358, V362, and S384;

(8) clone 8 consists of Q219, K221, I231, S235, T237, V238, K248, A258, 1264, K270, K282, L287, P299, and E351;

(9) clone 9 consists of M231, T246, A251, C263, G289, L307, L309, and E334;

(10) clone 10 consists of Q219, K221, I231, S235, T237, M238, V242, V246, K248, A258, 1264, K270, K282, L287, P299, A321, L322, S332, Q346, P347, T351, N358, V362, S384, insertion of GA between positions 407 and 408, N452, Y456, A457, K460, and E472; and

(11) clone 11 consists of insertion of GA between positions 407 and 408.

2. A method for the treatment of allergies in the triggering of which group 4 allergens of the *Poaceae* are involved in a subject in need thereof, comprising administering to said subject an effective amount of the polypeptide encoded by a DNA sequence which encodes an isolated polypeptide which comprises (a) a single nucleotide polymorph of the polynucleotide sequence of SEQ ID NO: 1, or (b) a single amino acid polymorph of the polypeptide sequence of SEQ ID NO: 2.

3. A method for the treatment of allergies in the triggering of which group 4 allergens of the *Poaceae* are involved in a subject in need thereof, comprising administering to said subject an effective amount of an immunomodulatory, T cell-reactive Phl p 4 polypeptide fragment encoded by a DNA sequence selected from the group consisting of (a) a DNA molecule encoding a polypeptide consisting of amino acids 1-200 of the polypeptide sequence of SEQ ID NO: 2, SEQ ID NO: 4, SEQ ID NO: 6 or a polypeptide variant consisting of the polypeptide sequence of SEQ ID NO: 2 with the amino acid variations of clones 1 to 11, wherein (1) clone 1 consists of L54, I57, V62, S76, T100, N107, Y137, P141, T142, K189, Q219, K221, L227, I231, S235, T237, V238, K248, A258, 1264, K270, K282, L287, P299, A321, L322, S332, Q346, P347, T351, L357, N358, V362, 5384, A410, D419, Y456, A457, K460, and E472;

(2) clone 2 consists of L54, I57, V62, T76, T100, N107, Y137, P141, T142, K189, Q219, K221, I231, S235, T237, V238, K248, A258, 1264, K270, K282, L287, P299, A321, L322, S332, Q346, P347, T351, L357, N358, V362, S384, A410, D419, Y456, A457, K460, and E472;

(3) clone 3 consists of P141, K282, L287, P299, L347, and E351;

(4) clone 4 consists of G289, A410, D419, Y456, A457, K460, and E472;

(5) clone 5 consists of L347, E351, S384, A410, D419, Y456, A457, K460, and E472;

(6) clone 6 consists of N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, and K460;

(7) clone 7 consists of K248, A258, I264, K270, K282, L287, P299, A321, L322, S332, Q346, P347, T351, L357, N358, V362, and S384;

(8) clone 8 consists of Q219, K221, I231, S235, T237, V238, K248, A258, I264, K270, K282, L287, P299, and E351;

(9) clone 9 consists of M231, T246, A251, C263, G289, L307, L309, and E334;

(10) clone 10 consists of Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, and E472; and

(11) clone 11 consists of insertion of GA between positions 407 and 408; and (b) a DNA molecule encoding a polypeptide consisting of amino acids 185-500 of the polypeptide sequence of SEQ ID NO: 2, SEQ ID NO: 4, SEQ ID NO: 6 or a polypeptide variant consisting of the polypeptide sequence of SEQ ID NO: 2 with the amino acid variations of clones 1 to 11, wherein (1) clone 1 consists of L54, I57, V62, S76, T100, N107, Y137, P141, T142, K189, Q219, K221, L227, I231, S235, T237, V238, K248, A258, I264, K270, K282, L287, P299, A321, L322, S332, Q346, P347, T351, L357, N358, V362, 5384, A410, D419, Y456, A457, K460, and E472;

(2) clone 2 consists of L54, I57, V62, T76, T100, N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, K460, and E472;

(3) clone 3 consists of P141, K282, L287, P299, L347, and E351;

(4) clone 4 consists of G289, A410, D419, Y456, A457, K460, and E472;

(5) clone 5 consists of L347, E351, S384, A410, D419, Y456, A457, K460, and E472;

(6) clone 6 consists of N107, Y137, P141, T142, K189, Q219, K221, I231, S235, T237, V238, K248, A258, I264, K270, K282, L287, P299, A321, L322, S332, Q346, P347, T351, L357, N358, V362, S384, A410, D419, Y456, A457, and K460;

(7) clone 7 consists of K248, A258, I264, K270, K282, L287, P299, A321, L322, S332, Q346, P347, T351, L357, N358, V362, and S384;

(8) clone 8 consists of Q219, K221, I231, S235, T237, V238, K248, A258, I264, K270, K282, L287, P299, and E351;

(9) clone 9 consists of M231, T246, A251, C263, G289, L307, L309, and E334;

(10) clone 10 consists of Q219, K221, I231, S235, T237, M238, V242, V246, K248, A258, I264, K270, K282, L287, P299, A321, L322, S332, Q346, P347, T351, N358, V362, S384, insertion of GA between positions 407 and 408, N452, Y456, A457, K460, and E472; and

(11) clone 11 consists of insertion of GA between positions 407 and 408.

* * * * *